(12) United States Patent
Harrell

(10) Patent No.: US 11,491,189 B2
(45) Date of Patent: *Nov. 8, 2022

(54) AMNIOTIC FLUID FORMULATION FOR TREATMENT OF LUNG DISORDERS

(71) Applicant: MAM HOLDINGS OF WEST FLORIDA, L.L.C., Tarpon Springs, FL (US)

(72) Inventor: Carl Randall Harrell, Tarpon Springs, FL (US)

(73) Assignee: MAM Holdings of West Florida, L.L.C., Tarpon Springs, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/876,988

(22) Filed: Jan. 22, 2018

(65) Prior Publication Data

US 2018/0140641 A1    May 24, 2018

Related U.S. Application Data

(63) Continuation of application No. 15/290,271, filed on Oct. 11, 2016, now abandoned.

(60) Provisional application No. 62/349,352, filed on Jun. 13, 2016.

(51) Int. Cl.
| | | |
|---|---|---|
| A61K 35/50 | (2015.01) | |
| A61H 23/02 | (2006.01) | |
| A61K 9/00 | (2006.01) | |
| A61P 11/06 | (2006.01) | |
| A61P 11/00 | (2006.01) | |
| A61K 45/06 | (2006.01) | |
| A61H 33/14 | (2006.01) | |

(52) U.S. Cl.
CPC ............. *A61K 35/50* (2013.01); *A61H 23/02* (2013.01); *A61K 9/0078* (2013.01); *A61K 45/06* (2013.01); *A61P 11/00* (2018.01); *A61P 11/06* (2018.01); *A61H 2033/143* (2013.01); *A61H 2205/084* (2013.01)

(58) Field of Classification Search
CPC ...... A61K 35/50; A61K 9/0078; A61K 45/06; A61P 11/00; A61P 11/06
See application file for complete search history.

(56) References Cited

U.S. PATENT DOCUMENTS

| | | | |
|---|---|---|---|
| 1,699,479 | A | 1/1929 | Scott |
| 3,752,158 | A | 8/1973 | Kariher |
| 4,308,875 | A | 1/1982 | Young |
| 4,977,897 | A | 12/1990 | Hurwitz |
| 5,000,192 | A | 3/1991 | Sealfon |
| 5,219,576 | A | 6/1993 | Chu |
| 5,436,135 | A | 7/1995 | Tayot |
| 5,698,228 | A | 12/1997 | Takai |
| 5,997,896 | A | 12/1999 | Carr, Jr. |
| 7,871,646 | B2 | 1/2011 | Ghinelli |
| 7,928,280 | B2 | 4/2011 | Hariri |
| 8,372,439 | B2 | 2/2013 | Daniel |
| 9,132,156 | B1 | 9/2015 | Werber |
| 9,579,350 | B1 | 2/2017 | Harrell |
| 9,884,078 | B2 | 2/2018 | Harrell |
| 2004/0057938 | A1 | 3/2004 | Ghinelli |
| 2004/0093046 | A1 | 5/2004 | Sand |
| 2005/0079147 | A1 | 4/2005 | Delaey |
| 2008/0064098 | A1 | 3/2008 | Allickson |
| 2008/0181935 | A1 | 7/2008 | Bhatia |
| 2008/0181967 | A1 | 7/2008 | Liu |
| 2008/0286378 | A1 | 11/2008 | Behrens |
| 2009/0054350 | A1 | 2/2009 | Tayot |
| 2010/0318048 | A1 | 12/2010 | Hoefinghoff |
| 2011/0269667 | A1 | 11/2011 | Shoseyov |

(Continued)

FOREIGN PATENT DOCUMENTS

| | | | |
|---|---|---|---|
| WO | | 2006091546 | 8/2006 |
| WO | WO 2006/108556 | | * 10/2006 |

(Continued)

OTHER PUBLICATIONS

Haygain USA, "The Evolvement of Flexineb Equine Nebulizers", Oct. 25, 2018, pp. 1-6, https://www.haygain.us/blogs/news-and-events/the-evolvement-of-flexineb-equine-nebulizers.*

Tang et al.; "Excess soluble vascular endothelial growth factor receptor-1 in amniotic fluid impairs lung growth in rats: linking preeclampsia with bronchopulmonary dysplasia" 2012; Am. J. Physiol. Lung Cell. Mol. Physiol.; 302:L36-L46; doi:10.1152/ajplung.00294.2011 (Year: 2012).*

Hallman et al.; "Isolation of Human Surfactant from Amniotic Fluid and a Pilot Study of Its Efficacy in Respiratory Distress Syndrome"; 1983; Pediatrics; 71(4):473-482 (Year: 1983).*

U.S. Appl. No. 15/053,497, filed Feb. 2016, Harrell.

Adzick, et al., "Cells, matrix, growth factors, and the surgeon. The biology of scarless fetal wound repair", Ann Surg, 220:10 8 (1994).

(Continued)

*Primary Examiner* — Timothy P Thomas
(74) *Attorney, Agent, or Firm* — McKee, Voorhees & Sease, PLC

(57) ABSTRACT

Formulations of human amniotic fluid and methods of use thereof for treatment of lung disorders, and/or injuries have been developed. The formulations are suitable for topical delivery to the lung for treatment of lung disorders including chronic obstructive pulmonary disorders (COPD), asthma, emphysema, bronchiectasis, chronic bronchitis, interstitial lung disease, alpha-1 antitrypsin emphysema, as well as for treatment of acute lung injuries. Methods including administering specifically formulated, diluted sterile de-cellularized human amniotic fluids topically to the lungs, preferably as aerosol droplets, are described. In particular, the methods involving administration of the amniotic fluid formulation in the form of aerosol droplets with size between about 1.5 μm to about 5 μm, preferably from about 2.5 μm to about 3.5 μm, inclusive, using apparatus such as high-efficiency vibrating mesh nebulizers, are described. Formulations described can treat, or prevent one or more symptoms of a chronic lung dis

(56) References Cited

U.S. PATENT DOCUMENTS

| | | | |
|---|---|---|---|
| 2012/0010727 A1 | 1/2012 | Young | |
| 2014/0336600 A1 | 11/2014 | Harrell | |
| 2015/0025366 A1 | 1/2015 | Harrell | |
| 2018/0271915 A1 | 9/2018 | Beaudry | |
| 2020/0129562 A1* | 4/2020 | Koob | A61M 5/31 |

FOREIGN PATENT DOCUMENTS

| | | | | |
|---|---|---|---|---|
| WO | WO2014/072468 | 5/2014 | ............ | A61K 35/12 |
| WO | 2015134936 | 9/2015 | | |
| WO | WO2015/134946 | 9/2015 | ............ | A61K 38/18 |
| WO | 2015199506 | 12/2015 | | |

OTHER PUBLICATIONS

Ainslie, "Inhalational injuries produced by smoke and nitrogen dioxide", G, Respir Med. 87(3):169-74(1993).
Anker, et al., "Amniotic fluid as a novel source of mesenchymal stem cells for therapeutic transplantation", Blood, 102:1548 9 (2003).
Baur, et al., "Output and aerosol properties of 5 nebulizer/compressor systems with arformoterol inhalation solution", Respiratory Care, 54(10:1342-7 (2009).
Bergeron, et al., "Airway remodeling in asthima: from benchside to clinical practice", Can Respir J., 17(4): e85-e93 (2010).
BIOSIS Database accession No. PREV200510252583, "Tropical application of amniotic fluid reduces corneal neovascularization after ocular alkali burn",1 page, appeared Apr. 1, 2004, retrieved Jul. 28, 2009.
Castro-Combs, et al., "Cornel wound healing is modulated by topical application of amniotic fluid in an exvivo organ culture model", Exp Eye Res., 87:56-63 (2008).
D'Agostino, et al., "Mesenchymal stem cell therapy for the treatment of chronic obstructive pulmonary disease", Expert Opin Biol Ther. 10(5):681-7 (2010).
Dua, et al., "A new classification of ocular surface burn", Br J Ophthalmol, 85:1379-83 (2001).
Duffy, et al., "Vascular Endothelial Growth Factor (VEGF) and Its Role in Non-Endothelial Cells: Auiocrine Signalling by VEGF", In: Madame Curie Bioscience Database [Internet]. Austin (TX): Landes Bioscience (2000).
Fletcher, et al., "The natural history of chronic airflow obstruction", Br Med J. 1:1645-8 (1977).
Gao, et al., "Effects of amniotic fluid on proteases: a possible role of amniotic fluid in fetal wound healin", Ann Plastic Surg, 33:128 34 (1994).
Gorguner, et al., "Acute inhalation injury", Eurasian J Med. 42(1):28-35(2010).
Gu,et al., "Mesenchymal stem cells alleviate airway inflammation and emphysema in COPD through down-regulation of cyclooxygenase-2 via p38 and ERK MARK pathways", Sci Rep. 5:8733 (2015).
Hartzell, "Overview of combustion toxicology", Toxicology., 115(1-3):7-23 (1996).
Herretes, et al., "Use of topical human amniotic fluid in the treatment of acute ocular alkali injuries in mice", Am J Ophthalmology, 142(2):271-8 (2006).
Hoeben, et al., "Vascular endothelial growth factor and angiogenesis", Pharmacol Rev, 56:549-80 (2004).
Hoyert, et al., "Deaths: preliminary date for 2011", Natl Vital Stat Rep. 61(6):1-65 (2012).
International Search Report and Written Opinion for PCT/US206/056231 dated Dec. 6, 2016.
International Search Report and Written Opinion for PCT/US206/056267 dated Dec. 7, 2016.
Kales, et al., "Acute chemical emergencies", N Engl J Med., 19; 350(8):800-8 (2004).
Karacal, et al., "Effe t of human amniotic fluid on bone healing", J Surg Res., 129(2):283-7 (2005).
Lee, et al, "Effect of amniotic fluid in corneal sensitivity and nerve regeneration after excimer laser ablation", Cornea, 15(5):517-24 (1996).
Maraldi, et al., "Rote of hepatocyte growth factor in the immunomodulation potential of amniotic fluid stem cells", Stem Cells Transl Med, 4(6):539-47 (2015).
Nagase, et al., "Structure and function of matrix metalloproteinases and TIMPs" Cardiovasc Res., 69(3): 562-73 (2006).
Nemery, "Metal toxicity and the respiratory tract", Eur Respir J. 3(2):202-19 (1990).
Newman, et al., "Occupational illness", N Engl J Med. 26; 333(17):1128-34 (1995).
Ozgenel, et al., "Effect of human amniotic fluid on peritendinous adhesion formation and tendon healing after flexor tendon surgery in rabits", J Hand Surg., 26(2):332-9 (2001).
Ozgenel, et al., "Effects of human amniotic fluid on cartilage regeneration from free perichondrial grafts in rabits", British J Plastic Surg., 57(5):423-8 (2004).
Ozgenel, et al., "Effects of human amniotic fluid on peripheral nerve scarring and regeneration to rats", J Neurosurg, 98:371 7 (2003).
Sporn, et al., "Transforming growth factor-beta: biological junction and chemical structure", Science, 233(4763) 532-4 (1986).
Todderud, et al., "Epidermal growth factor: the receptor and its function", Biofactors., 2(1):11-5 (1989).
Weiss, et al., "placebo-controlled, randomized trial of mesenchymal stem cells in COPD", Chest. 143(6): 1590-8 (2013).
Woode, et al., "Collagenolytic matrix metalloproteinases in chronic obstructive lung disease and cancer", Cancers, 7(1): 329-341 (2015).
Yun, et al., "Fibroblast growth factors: biology, function, and application for tissue regeneration", J Tissue Eng , 218142, doi:1-18 (2010).
Hallman, et al., "Isolation of Human Surfactant from Amniotic Fluid and Pilot Study of Its Efficacy in Respiratory Distress Syndrome", Pediatrics, American Academy of Pediatrics, 71(4):473-482 (1983).
Rubin, et al., "Emerging aerosol drug delivery strategies: From bench to clinic", Advanced Drug Delivery Reviews, 75:141-48 (2014).
Yu, et al., "Wnt4 signaling prevents skeletal aging and inflammation by inhibiting nuclear factor-kB", Nature Medicine, 20(9):1009-1101 (2014).

* cited by examiner

AMNIOTIC FLUID FORMULATION FOR TREATMENT OF LUNG DISORDERS

CROSS-REFERENCE TO RELATED APPLICATIONS

This application claims benefit of U.S. Provisional Application No. 62/349,352, filed Jun. 13, 2016, which is incorporated by reference in its entirety.

FIELD OF THE INVENTION

The invention relates to the treatment, or prevention of pulmonary diseases, particularly by administration to the lung a formulated amniotic fluid solution via a nebulizer.

BACKGROUND OF THE INVENTION

Good lung health contributes significantly to a person's quality of life and their ability to perform common daily activities such as walk, exercise, and sleep, and to carry out simple functions in their routine environment.

In the past few decades, the prevalence of asthma has almost doubled, and today asthma affects 8-10% of the world's population (Centers for Disease Control and Prevention, *Vital Signs*, May 2011). Asthma is a chronic inflammatory disorder of the airways and is characterized by airway hyperresponsiveness (AHR) to nonspecific stimuli and airway remodeling, which is associated with alterations in the structures and functions of the principal components of the airway, including fibroblasts, and myofibroblasts (Bergeron C et al., *Can Respir J.* 17(4): e85-e93 (2010)). Asthma is broadly classified into bronchial asthma and cardiac asthma, but in general "asthma" refers to simply bronchial asthma.

Another representative pulmonary disease is chronic obstructive pulmonary disease (COPD). COPD is distinguished from asthma by accompanying obstruction of airway, and COPD was the third leading cause of death in the United States in 2011. More than 11 million people have been diagnosed with COPD, but an estimated 24 million may have the disease without even knowing it (Hoyert D L et al., *Natl Vital Stat Rep.* 61(6):1-65 (2012)).

COPD causes serious long-term disability, and can be a cause of early death. COPD is characterized by irreversible airflow limitation due to obstruction in the small conducting airways and emphysematous destruction of the gas exchanging surface of the lung. Tobacco smoke is the major risk factor for COPDs with up to 10-20% of smokers developing this disease (Fletcher C et al., *Br Med J.* 1:1645-8 (1977)). COPD is exemplified by chronic obstructive bronchitis, chronic bronchiolitis and emphysema. Current theories concerning pathogenesis of COPD include an imbalance between protease and anti-protease activity, and induced apoptosis of alveolar wall cells. Deregulation of pathways involved in oxidative stress, angiogenesis, and chronic inflammation, and aberrant tissue remodeling and repair processes lead to the destruction of the extracellular matrix (ECM) in the lung (Woode D et al., *Cancers,* 7(1): 329-341 (2015)) However, the etiology of the initiation and progression of COPD remain poorly understood.

Treatment options of asthma and chronic obstructive pulmonary diseases are very limited, and have mostly depended on using anti-inflammatory agents or bronchodilators. At this time there is no cure for COPD, and the rate of mortality associated with COPD continues to increase worldwide.

There is a need for effective treatment for patients with asthma, COPD and other obstructive or restrictive lung disorders.

Recent wars have created an entire class of individuals with a variety of lung injuries, including inhalation damage, burns and as a byproduct of trauma. For example, military personnel deployed to Iraq and Afghanistan, from 2004 to the present, served in a setting of unique environmental conditions. Among these are exposures to burning trash in open air "burn pits" lit on fire with jet fuel JP-8. Depending on trash burned—water bottles, styrofoam trays, medical waste, unexploded munitions, and computers—toxins may be released such as dioxins and n-hexane and benzene. Particulate matter air pollution culminates from these fires and fumes. Additional environmental exposures include sandstorms which differ in direction and relationship to rain. These wars saw the first use of improvised explosive devices (roadside phosphate bombs), as well as vehicle improvised explosive devices (car bombs), which not only potentially aerosolize metals, but also create shock waves to induce lung injury via blast overpressure. Conventional mortar rounds are also used by Al Qaeda in both Iraq and Afghanistan. Outdoor aeroallergens from date palm trees are prevalent in southern Iraq by the Tigris and Euphrates rivers, while indoor aeroallergen *aspergillus* predominates during the rainy season. High altitude lung disease may also compound the problem, particularly in Kandahar, Afghanistan. Clinically, soldiers may present with new-onset asthma or fixed airway obstruction. Some have constrictive bronchiolitis and vascular remodeling on open lung biopsy—despite having normal spirometry and chest x-rays and CT scans of the chest. Others have been found to have titanium and other metals in the lung (rare in nature). Still others have fulminant biopsy-proven sarcoidiosis.

Therefore, it is an objective of the current invention to provide formulations for the treatment and prevention of a variety of lung disorders.

It is also an objective of the current invention to provide methods for effective administration of the formulation to the lung.

SUMMARY OF THE INVENTION

Formulations of sterile human amniotic fluid and methods of use thereof have been developed. The formulations are devoid of amniotic cells, elements of micronized membrane, and chorion particles. The formulations are not heat treated or treated with ethidium oxide. The formulations are suitable for topical delivery to the lung, for treatment and/or prevention of lung disorders including chronic obstructive pulmonary disorders (COPD), asthma, emphysema, bronchiectasis, chronic bronchitis, interstitial lung disease, alpha-1 antitrypsin emphysema, as well as for treatment and/or prevention of acute lung injuries resulting from exposure to chemical irritants, asphyxiants, burns and smokes, chemical warfare and riot control agents, toxic metals, and/or blast injuries.

The formulations of amniotic fluid are topically delivered to the surface of the lung to alleviate or prevent at least one symptom of a lung disorder/injury. In particular, the amniotic fluid formulations are effective in improving exercise endurance, increasing baseline blood oxygen saturation, and/or reducing inflammation in the lungs.

Methods including administering specifically formulated sterile decellularized human amniotic fluid to the lungs, preferably as aerosol or nebulized droplets or spray, are described. Methods for effective delivery of amniotic fluid formulations to target the distal regions of the lung use apparatus such as nebulizers. Typically, formulations of amniotic fluids are administered using nebulizers that allow the generation of aerosol droplets with size between about 1.5 µm to about 5 µm, for example from about 2.5 µm to about 3.5 µm, inclusive. Some exemplary nebulizers include high-efficiency jet nebulizers, high-efficiency ultrasonic nebulizers, or high-efficiency vibrating mesh nebulizers. These devices enable the efficient delivery of the amniotic fluid formulation to the distal regions of the lung.

Dosage units of amniotic fluid formulations for treatment of lung disorders or lung injuries are also provided. Generally, formulations of amniotic fluids are in a dosage unit from about 0.1 cc to about 10.0 cc, inclusive. In some embodiments, the D-HAF is diluted with sterile water, saline or buffer in a volume of about 0.1 cc to about 10.0 cc, inclusive.

Methods for treating lung disorders or lung injuries using the formulation in combination with one or more therapeutic, prophylactic or diagnostic agents are also described. In some embodiments, the one or more agents are bronchodilators, corticosteroids, methylxanthines, phosphodiesterase-4 inhibitors, anti-angiogenesis agents, antimicrobial agents, antioxidants, anti-inflammatory agents, growth factors, immunosuppressant agents, anti-allergic agents, or combinations thereof.

A kit containing one or more single, sterile units of D-HAF in fluid or solid form, and instructions on how the dose is to be used in a nebulizer or aerosolizer for treatment of lung disorders or lung injuries is also provided. The kit can also include a unit dose of sterile water, saline or buffer for dilution. The kit is generally used by practitioners for patients with a lung disorder including chronic obstructive pulmonary disorders (COPD), asthma, emphysema, bronchiectasis, chronic bronchitis, interstitial lung disease, alpha-1 antitrypsin emphysema, or combinations thereof. The kit can also be used for patients with acute lung injuries resulting from exposure to chemical irritants, asphyxiants, burns and smokes, chemical warfare and riot control agents, toxic metals, and/or blast injuries.

DETAILED DESCRIPTION OF THE INVENTION

I. Definitions

The term "Active Agent," refers to a physiologically or pharmacologically active substance that acts locally and/or systemically in the body. An active agent is a substance that is administered to an individual for the treatment (e.g., therapeutic agent), prevention (e.g., prophylactic agent), or diagnosis (e.g., diagnostic agent) of a disease or disorder. Active agents may also include materials that alleviate symptoms such as shortness of breath. The phrase "therapeutically effective amount" refers to an amount of the therapeutic agent that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation. A prophylactic agent refers to an agent that may prevent a disorder, disease or condition.

The term "tissue repair", refers to the restoration of tissue architecture and function after an injury in the context of the healing of damaged tissue. It encompasses cellular regeneration. Regeneration refers to a type of healing in which new growth restores portions of damaged tissue to an improved state, or to their normal state. Tissue regeneration can be initiated by stimulants in the formulations, and/or by stem cells introduced onto the damaged tissues.

The term "treating" refers to preventing or alleviating one or more symptoms of a disease, disorder or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The terms "enhance", "increase", "stimulate", "promote", "decrease", "inhibit" or "reduce" are used relative to a control. Controls are known in the art. For example, an increase response in a subject or cell treated with a compound is compared to a response in subject or cell that is not treated with the compound.

The term "growth factors," refers to a group of proteins or hormones that stimulate the cellular growth. Growth factors play an important role in promoting cellular differentiation and cell division, and they occur in a wide range of organisms.

The term "biocompatible" or "biologically compatible," generally refers to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "biodegradable" as used herein means that the materials degrades or breaks down into its component subunits, or digestion, e.g., by a biochemical process, of the material into smaller (e.g., non-polymeric) subunits.

The term "pharmaceutically acceptable," refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "molecular weight," generally refers to the relative average chain length of the bulk polymer or protein, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

II. Compositions

Formulations of purified human amniotic fluid are provided. Typically, the formulations include sterile de-cellularized human amniotic fluid (D-HAF), either in fluid form or solid form, for example, lyophilized powder, alone or in combination with appropriate excipients. Other active agents can be included. D-HAF contains over 300 human growth factors, some in amounts less than those found in natural amniotic fluid. D-HAF is devoid of amniotic cells and elements of micronized membrane or chorion particles.

Methods of preparing sterile de-cellularized amniotic fluid are described in detail in U.S. application Ser. No. 15/053, 497. D-HAF is sterilized by filtration, not irradiation, ethidium oxide or heat.

A. Amniotic Fluid

Amniotic fluid ("AF") contains nutrients and growth factors that facilitate fetal growth, provides mechanical cushioning and antimicrobial effectors that protect the fetus, and allows assessment of fetal maturity and disease. AF typically contains mixtures of growth factors, pro-inflammatory cytokines and anti-inflammatory cytokines, as well as a variety of macromolecules including carbohydrates, proteins and peptides, lipids, lactate, pyruvate, electrolytes, enzymes, and hormones.

In some embodiments, the formulation is not heat-treated, chemical-treated, fractionated relative to the raw fluid directly collected from the source. In some embodiments, the formulation retains more than 50%, more than 60%, more than 70%, more than 80%, or preferably more than 90%, of the amniotic factors present in the raw fluid. In some embodiments, the formulations are not diluted with any additional solution. In other embodiments, the formulations are not concentrated relative to the raw fluid. In some embodiments, the formulations are diluted just prior to being added into the nebulizer for use.

1. Growth Factors, Cytokines and Other Molecules

Growth factors and their receptors control a wide range of biological functions, regulating cellular proliferation, survival, migration and differentiation. Growth factors found in AF play a critical role in fetal growth and development.

A non-limiting list of growth factors that have been identified in AF includes such as epidermal growth factor (EGF), insulin-like growth factor I (IGF-I), vascular endothelial growth factor A (VEGF-α), tumor necrosis factor A (TNF-α), hepatocyte growth factor (HGF), fibroblast growth factor 7 (FGF7), matrix metallopeptidase (MMP-9), granulocyte-colony stimulating factor (GCSF), matrix metalloproteinase-7 (MMP-7), matrix metalloproteinase-7 (MMP-13), transforming growth factor alpha (TGF-α), transforming growth factor beta (TGF-β), fibroblast growth factor 4 (FGF-4), endocrine gland-derived vascular endothelial growth factor (EG-VEGF), interleukin 8 (IL-8), fibroblast growth factor 21 (FGF-21), angiopoietin-2 (ANG2), Glial cell-derived neurotrophic factor (GDNF), fibroblast growth factor 19 (FGF-19), TIMP metallopeptidase inhibitor 2 (TIMP-2), angiopoietin-1 (ANG-1), Transforming growth factor beta 1 (TGFβ1), macrophage colony-stimulating factor (M-CSF), angiotensinogen, platelet derived growth factor-AA (PDGF-AA), and stem cell factor (SCF).

Epidermal growth factor (EGF) is a small polypeptide hormone with mitogenic properties in vivo and in vitro. EGF elicits biologic responses by binding to a cell surface receptor which is a transmembrane glycoprotein containing a cytoplasmic protein tyrosine kinase. EGF responses are mediated by ligand binding and activation of this intrinsic protein kinase. The receptor can be phosphorylated by other protein kinases, and this may regulate receptor function. Stimulation of the receptor tyrosine kinase activity by ligand binding must regulate the activity of an as yet undefined molecule(s) responsible for transmitting a mitogenic signal to the nucleus (Todderud G, et al., Biofactors. 1989, 2(1): 11-5).

Vascular endothelial growth factor (VEGF), also known as vascular permeability factor (VPF), was originally described as an endothelial cell-specific mitogen. VEGF is produced by many cell types including tumor cells, macrophages, platelets, keratinocytes, and renal mesangial cells. The activities of VEGF are not limited to the vascular system; VEGF plays a role in normal physiological functions such as bone formation, hematopoiesis, wound healing, and development (Duffy A M et al., In: Madame Curie Bioscience Database [Internet]. Austin (Tex.): Landes Bioscience (2000)).

TGF-α has a structure similar to EGF and binds to the same receptor. The amnion cells of the umbilical cord express EGF, TGF-α, and the functional EGF/TGF-α receptor, suggesting the possibility of a regulating role of the amnion in fetal growth and development. EGF and TGF-α have also been shown to stimulate the production of surfactant components. TGFβ1 is believed to induce terminal differentiation of intestinal epithelial cells and to accelerate the rate of healing of intestinal wounds by stimulating cell migration. TGFβ1 may also stimulate IgA production. VEGF-A is a signal protein that stimulates vasculogenesis and angiogenesis (Hoeben Am, et al., *Pharmacol Rev* 2004, 56:549-580).

Transforming growth factor-beta (TGF-β) is a multifunctional peptide that controls proliferation, differentiation, and other functions in many cell types. Many cells synthesize TGF-beta and essentially all of them have specific receptors for this peptide. TGF-beta regulates the actions of many other peptide growth factors and determines a positive or negative direction of their effects (Sporn M B, et al., Science 1986, 233(4763) 532-534).

Hepatocyte growth factor (HGF), the ligand for the receptor tyrosine kinase encoded by the c-Met proto-oncogene, is a multidomain protein structurally related to the pro-enzyme plasminogen and with major roles in development, tissue regeneration and cancer. A recent study showed its immunomodulation potential of amniotic fluid stem cells (Maraldi T, et al. *Stem Cells Transl Med,* 4(6):539-47 (2015)).

Fibroblast growth factors (FGFs) that signal through FGF receptors (FGFRs) regulate a broad spectrum of biological functions, including cellular proliferation, survival, migration, and differentiation. The FGF signal pathways are the RAS/MAP kinase pathway, PI3 kinase/AKT pathway, and PLCγ pathway, among which the RAS/MAP kinase pathway is known to be predominant. Several studies have recently implicated the in vitro biological functions of FGFs for tissue regeneration. Many current applications of FGF are in regeneration of tissues, including skin, blood vessel, muscle, adipose, tendon/ligament, cartilage, bone, tooth, and nerve tissues (Yun Y R, et al., J Tissue Eng 2010: 1(1)).

Matrix metalloproteinases (MMPs), also called matrixins, function in the extracellular environment of cells and degrade both matrix and non-matrix proteins. They play central roles in morphogenesis, wound healing, tissue repair and remodeling in response to injury, e.g. after myocardial infarction, and in progression of diseases such as atheroma, arthritis, cancer and chronic tissue ulcers. They are multi-domain proteins and their activities are regulated by tissue inhibitors of metalloproteinases (TIMPs) (Nagase H, et al., Cardiovascular Research, European Society of Cardiology, 562-573 (2006)).

Amniotic fluid also contains many pro- and anti-inflammatory cytokines. Pro- and anti-inflammatory cytokines play important immunoregulatory roles. Inflammation is characterized by interplay between pro- and anti-inflammatory cytokines. Cytokines are commonly classified in one or the other category: interleukin-1 (IL-1), tumor necrosis factor (TNF), gamma-interferon (IFN-gamma), IL-12, IL-18 and granulocyte-macrophage colony stimulating factor are well characterized as pro-inflammatory cytokines whereas IL4, IL-10, IL-13, IFN-alpha and transforming growth factor-beta are recognized as anti-inflammatory cytokines.

Exemplary pro-inflammatory cytokines include Eotaxin-2 (CCL24), interleukin 6 (IL-6), pulmonary and activation-regulated chemokine PARC or chemokine (C-C motif) ligand 18 (CCL18), total GRO which consisted of three subunits GROα/CXCL1, GROβ/CXCL2, and GROγ/CXCL3, expression of the neutrophil-activating CXC chemokine (ENA-78/CXCL-5), chemokine (C-C motif) ligand 21 (CCL21 or 6Ckine), macrophage inflammatory protein 3 alpha (MIP-3α or CCL20), monokine induced by gamma (MIG or CXCL-9), MIP-1α, chemokine (C-C motif) ligand 5 (CCL-5), also known as RANTES (regulated on activation, normal T cell expressed and secreted), Interleukin-1 alpha (IL-1α), macrophage inflammatory protein-1β (MIP-1β or CCL4), tumor necrosis factor (TNFα) and monocyte chemotactic protein 2 (MCP-2 or CCL8).

Exemplary anti-inflammatory cytokines include the anti-inflammatory factors include interleukin 8 (IL-8), interleukin 13 (IL-13), interleukin 27 (IL-27), cytotoxic T-lymphocyte-associated protein 4 (CTLA-4), vascular endothelial growth factor D (VEGF-D), interleukin-1 receptor antagonist (IL-1Ra), transforming growth factor beta 1 (TGFβ1), interleukin 5 (IL-5) and interleukin 21 (IL-21).

2. Sources of Amniotic Fluid Formulations

The sterile amniotic fluid formulations are prepared from human amniotic fluid obtained from a pregnant woman. Human AF is obtained from patients who are undergoing amniocentesis, patients who are undergoing a Caesarean section delivery, and patients undergoing normal delivery using a specially designed receptacle to collect the fluid after rupture of membranes.

The de-cellularized human amniotic fluid (D-HAF) formulations can be stored for long periods of time, allowing for a broad range of application methods, including distribution and storage as aerosols, solutions, powders, etc. The sterile D-HAF can be refrigerated at about 1° C. to about 10° C. for long-term storage. In one embodiment, the sterile D-HAF is refrigerated at 4° C. for up to 12 months and more. Preferably, the long-term storage does not reduce the quantity of the total soluble proteins or factors present in the D-HAF. For some embodiments, the total soluble proteins retained after long-term storage in refrigerated conditions is about 10%, 20%, 30%, 40%, 50%, 60%, 70%, 80%, or 90% of the fresh D-HAF.

D-HAF formulations containing amniotic factors can be supplied as a clear one-part solution in a suitable container for storage at 4° C., or for storage at −20° C., or at −80° C. For example, liquid formulations in prefilled aliquots can be suitable for storage at 1-5° C., or for storage at −20° C., or at −80° C. The liquid formulation can be suitable for topical application in a nebulizer or an inhaler. In other embodiments, the fluid can be supplied as a kit that can be stored at 4° C., at −20° C., or at −80° C. until needed.

In some embodiments, D-HAF formulations use a final filtration through 0.2 μm to get the best sterility assurance level and produce a sterile amniotic fluid without any irradiation. In some embodiments, D-HAF formulations have a $10^{-6}$ sterility assurance level without irradiation. In other embodiments, lyophilisate derived from amniotic fluid through lyophilization may be irradiated by e-beam irradiation or gamma ray irradiation to add another guarantee for the final sterility of the powder.

In some embodiments, D-HAF formulations are synthesized amniotic fluid to include all the known amniotic factors for the same therapeutic, and/or prophylactic properties in treating lung disorders.

In further embodiments, amniotic fluid can be collected from animal sources, for example from horses, pigs, buffalos etc. Once amniotic fluid is collected from any source, a similar sterile process of de-cellularizing the fluid by a series of centrifugation and filtration can be carried. Although the sources of the amniotic fluid do not dictate the recipient of these formulations it is generally preferred that it is sourced from a donor of the same species as the recipient. For example, horses can use amniotic fluid formulations for treating, or preventing pulmonary disorders or injuries by using formulations prepared from equine amniotic fluid. However, the uses of any amniotic fluid, specially human amniotic fluid formulations, are not limited to the same species as the donor.

B. Additional Therapeutic, Prophylactic or Diagnostic Agents

In addition to the amniotic fluid component, the formulation can contain one or more additional therapeutic, diagnostic, and/or prophylactic agents. In some embodiments, the composition may contain one or more additional compounds to relief symptoms such as inflammation, or shortness of breath. Representative therapeutic (including prodrugs), prophylactic or diagnostic agents can be peptides, proteins, carbohydrates, nucleotides or oligonucleotides, small molecules, or combinations thereof. Non-limiting examples include a bronchodilator, a corticosteroid, a methylxanthine, a phosphodiesterase-4 inhibitor, an antimicrobial agent, an analgesic, a local anesthetic, an anti-inflammatory agent, an immunosuppressant agent, an anti-angiogenesis agent anti-allergenic agent, an enzyme cofactor, an essential nutrient and a growth factor.

The active agents can be a small molecule active agent or a biomolecule such as an enzyme or protein, polypeptide, lipid, lipoprotein or nucleic acid. Suitable small molecule active agents include organic and organometallic compounds. In some instances, the small molecule active agent has a molecular weight of less than about 2000 g/mol, more preferably less than about 1500 g/mol, most preferably less than about 1200 g/mol. The small molecule active agent can be a hydrophilic, hydrophobic, or amphiphilic compound.

In some cases, one or more additional active agents may be encapsulated in, dispersed in, or otherwise associated with particles in the formulation. In certain embodiments, one or more additional active agents may also be dissolved or suspended in the pharmaceutically acceptable carrier.

In the case of pharmaceutical compositions for the treatment of lung diseases, the formulation may contain one or more therapeutic agents to treat, prevent or diagnose a disease or disorder of the lung. Non-limiting examples of therapeutic agents include bronchodilators, corticosteroids, methylxanthines, phosphodiesterase-4 inhibitors, anti-angiogenesis agents, antibiotics, antioxidants, anti-viral agents, anti-fungal agents, anti-inflammatory agents, growth factors, immunosuppressant agents, anti-allergic agents, and combinations thereof.

The amount of a second therapeutic generally depends on the severity of lung disorders to be treated. Specific dosages can be readily determined by those of skill in the art. See Ansel, Howard C. et al. *Pharmaceutical Dosage Forms and Drug Delivery Systems* (6$^{th}$ ed.) Williams and Wilkins, Malvern, Pa. (1995). Alternatively, the amniotic formulation can be used in combination with cell delivery, for example, the delivery of stem cells, pluripotent cells, somatic cells, or combinations thereof.

In other embodiments, one or more agents include a bronchodilator, a corticosteroid, a methylxanthine, a phosphodiesterase-4 inhibitor, an antimicrobial agent, an analgesic, a local anesthetic, an anti-inflammatory agent, an immunosuppressant agent, an anti-angiogenesis agent antiallergenic agent, an enzyme cofactor, an essential nutrient and a growth factor are administered prior to, in conjunction with, subsequent to, or alternation with treatment with the described amniotic fluid formulation.

The additive drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704.

In some cases, the additional agent is a diagnostic agent imaging or otherwise assessing the site of application. Exemplary diagnostic agents include paramagnetic molecules, fluorescent compounds, magnetic molecules, and radionuclides, x-ray imaging agents, and contrast media. These may also be ligands or antibodies which are labelled with the foregoing or bind to labelled ligands or antibodies which are detectable by methods known to those skilled in the art.

In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic.

In some embodiments, the amniotic fluid formulation is used in combination with oxygen therapy.

1. Bronchodilators

In some embodiments, amniotic fluid formulations are used in combination with one or more bronchodilators. Bronchodilators are a type of medication that helps open the airways to make breathing easier.

Short-acting bronchodilators in an emergency situation or as needed for quick relief. Some exemplary short-acting bronchodilators include anticholinergics such as ipratropium (e.g. ATROVENT®, in COMBIVENT®, in DUONEB®), beta2-agonists such as albuterol (e.g. VOSPIRE ER®, in COMBIVENT®, in DUONEB®), and levalbuterol (e.g. XOPENEX®).

Long-acting bronchodilators are used to treat COPD over an extended period of time. They are usually taken once or twice daily over a long period of time, and they come as formulations for inhalers or nebulizers. Some exemplary long-acting bronchodilators include anticholinergics such as aclidinium (e.g. TUDORZA®), tiotropium (e.g. SPIRIVA®), or umeclidinium (e.g. INCRUSE ELLIPTA®), beta2-agonists such as arformoterol (e.g. BROVANA®), formoterol (e.g. FORADIL®, PERFOROMIST®), indacaterol (e.g. ARCAPTA®), salmeterol (e.g. SEREVENT®), and olodaterol (e.g. STRIVERDI RESPIMAT®).

2. Corticosteroids

In some embodiments, amniotic fluid formulations are used in combination with one or more corticosteroids. Corticosteroids help reduce inflammation in the body, making air flow easier to the lungs. There are several corticosteroids. Some are prescribed with bronchodilators because these two medications can work together to make breathing more effective. Fluticasone (e.g. FLOVENT®), budesonide (e.g. PULMICORT®), and prednisolone are the ones doctors commonly prescribe for COPD.

3. Methylxanthines

In some embodiments, amniotic fluid formulations are used in combination with one or more methylxanthines. Some people have severe difficulty with COPD and the regular or first-line treatments alone don't seem to help. In these cases, theophylline (e.g. THEO-24®, THEOLAIR®, ELIXOPHYLLINE®, QUIBRON-T®, UNIPHYL®, and ELIXOPHYLLIN®), can be used, which works as an anti-inflammatory and relaxes the muscles in the airway, to take along with a bronchodilator. Theophylline comes as a pill or a liquid to be taken on a daily basis, and/or combined with other medications.

4. Phosphodiesterase-4 Inhibitors

In some embodiments, amniotic fluid formulations are used in combination with one or more phosphodiesterase-4 inhibitors. This medication helps relieve inflammation, which can improve air flow to the lungs. Roflumilast (e.g. DALIRESP®) is a phosphodiesterase-4 inhibitor and comes as a pill that can be taken once per day. It is usually prescribed along with a long-acting bronchodilator.

5. Antimicrobial Agents

In some embodiments, amniotic fluid formulations are used in combination with one or more antimicrobial agents. An antimicrobial agent is a substance that kills or inhibits the growth of microbes such as bacteria, fungi, viruses, or parasites. Antimicrobial agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines.

Other exemplary antimicrobial agents include iodine, silver compounds, moxifloxacin, ciprofloxacin, levofloxacin, cefazolin, tigecycline, gentamycin, ceftazidime, ofloxacin, gatifloxacin, amphotericin, voriconazole, natamycin.

6. Local Anesthetics

In some embodiments, amniotic fluid formulations are used in combination with one or more local anesthetics. A local anesthetic is a substance that causes reversible local anesthesia and has the effect of loss of the sensation of pain. Non-limiting examples of local anesthetics include ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and any combination thereof. In other aspects of this embodiment, the amniotic fluid formulations comprises an anesthetic agent in an amount of, e.g., about 10 mg, about 50 mg, about 100 mg, about 200 mg, or more than 200 mg. The concentration of local anesthetics in the compositions can be therapeutically effective meaning the concentration is adequate to provide a therapeutic benefit without inflicting harm to the patient.

7. Anti-inflammatory Agents

In some embodiments, amniotic fluid formulations are used in combination with one or more anti-inflammatory agents. Anti-inflammatory agents reduce inflammation and include steroidal and non-steroidal drugs. Suitable steroidal active agents include glucocorticoids, progestins, mineralocorticoids, and corticosteroids. Other exemplary anti-inflammatory agents include triamcinolone acetonide, fluocinolone acetonide, prednisolone, dexamethasone, loteprendol, fluorometholone, ibuprofen, aspirin, and naproxen. Exemplary immune-modulating drugs include cyclosporine, tacrolimus and rapamycin. Exemplary non-steroidal anti-inflammatory drugs (NSAIDs) include mefenamic acid, aspirin, Diflunisal, Salsalate, Ibuprofen, Naproxen, Fenoprofen, Ketoprofen, Deacketoprofen, Flurbiprofen, Oxaprozin, Loxoprofen, Indomethacin, Sulindac, Etodolac, Ketorolac, Diclofenac, Nabumetone, Piroxicam, Meloxicam, Tenoxicam, Droxicam, Lornoxicam, Isoxicam, Meclofenamic acid, Flufenamic acid, Tolfenamic acid, elecoxib, Rofecoxib, Valdecoxib, Parecoxib, Lumiracoxib, Etoricoxib, Firocoxib, Sulphonanilides, Nimesulide, Niflumic acid, and Licofelone.

In some embodiments, anti-inflammatory agents are anti-inflammatory cytokines. Exemplary cytokines are IL-10, TGF-β and IL-35. Anti-inflammatory cytokines in the context of biomaterial implant, skin grafts, and hair grafts are cytokine that induce an anti-inflammatory immune environment or suppress inflammatory immune environment. Activation of regulatory T cells, Tregs, is involved in the prevention of rejection, the induction and maintenance of peripheral tolerance of the allograft. Th17 cells are a subset of T helper cells which is characterized by the production of IL-17. Th17 cells have been suggested to play a role in allograft rejection. In some embodiments, cytokines to be added to the amniotic fluid formulations are those that induce Tregs activation (e.g. IL-25) and suppress Th17 activation (e.g. IL-10) for minimizing rejection.

8. Cells

In some embodiments, the amniotic fluid formulation further comprises at least one eukaryotic cell type. Some exemplary eukaryotic cell types include stem cells, immune cells such as T lymphocytes, B lymphocytes, natural killer cells, and dendritic cells, or combinations thereof.

Bone marrow-derived mesenchymal stem cells (MSCs) have been identified as one possible strategy for the treatment of chronic obstructive pulmonary disease (COPD) (Gu W et al., *Sci Rep.* 5:8733 (2015); Weiss D J et al., *Chest.* 143(6):1590-8 (2013); D'Agostino B et al., *Expert Opin Biol Ther.* 10(5):681-7 (2010)). In some embodiments, the stem cells are mesenchymal stem cells. Functional characteristics of mesenchymal stem cells that may benefit wound healing include their ability to migrate to the site of injury or inflammation, participate in regeneration of damaged tissues, stimulate proliferation and differentiation of resident progenitor cells, promote recovery of injured cells through growth factor secretion and matrix remodeling, and exert unique immunomodulatory and anti-inflammatory effects.

In certain embodiments, the mesenchymal stem cells protect lung tissue through suppression of pro-inflammatory cytokines, and through triggering production of reparative growth factors.

9. Other Agents

In some embodiments, amniotic fluid formulations are used in combination with one or more growth factors. Growth factor, also known as a cytokine, refers to a protein capable of stimulating cellular growth, proliferation, and/or cellular differentiation. Non-limiting examples of growth factors include transforming growth factor beta (TGF-β), transforming growth factor alpha (TGF-α), granulocyte-colony stimulating factor (GCSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF8), growth differentiation factor-9 (GDF9), acidic fibroblast growth factor (aFGF or FGF-1), basic fibroblast growth factor (bFGF or FGF-2), epidermal growth factor (EGF), vascular endothelial growth factor (VEGF) and hepatocyte growth factor (HGF).

In some embodiments, the formulation can include antibodies, including, for example, daclizumab, bevacizumab (Avastin®), ranibizumab (Lucentis®), basiliximab, ranibizumab, and pegaptanib sodium or peptides like SN50, and antagonists of NF.

In further embodiments, the formulation can include oligonucleotides. Representative oligonucleotides include siRNAs, microRNAs, DNA, and RNA. Oligonucleotides can be used as gene therapy complementing the efficacy of the amniotic fluid formulations.

In some embodiments, the amniotic fluid formulation further comprises one or more enzyme cofactors, and/or one or more essential nutrients. Exemplary cofactors include vitamin C, biotin, vitamin E, and vitamin K. Exemplary essential nutrients are amino acids, fatty acids, etc.

In some embodiments, the amniotic fluid formulation further comprises anti-proliferative drugs such as paclitaxel and derivatives. Representative anti-proliferative drugs include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarb amide, idarubicin, ifosfamide, innotecan, leucovorin, liposomal doxorubicin, liposomal daunorubici, lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposide, tegafur-uracil, temozolomide, teniposide, thiotepa, tioguanine, topotecan, treosulfan, vinblastine, vincristine, vindesine, vinorelbine, taxol and derivatives thereof, trastuzumab (HERCEPTIN®), cetuximab, and rituximab (RITUXAN® or MABTHERA®), bevacizumab (AVASTIN®), and combinations thereof. Representative pro-apoptotic agents include, but are not limited to, fludarabinetaurosporine, cycloheximide, actinomycin D, lactosylceramide, 15d-PGJ(2)5 and combinations thereof.

C. Dosage Formulations

Typically, amniotic fluid formulations are packaged into sterile dosage units which can be stored and distributed for use by attending physicians. Lyophilized or fluid formulations can be in the form of sterile packaged ampoule ready for use with a nebulizer.

The fluid dosages for use are raw amniotic fluids that are devoid of cells and particulate matter via a series of centrifugation and filtration steps. The concentrations of proteins, lipids, or any other molecules present in the de-cellularized human amniotic fluid are similar to that of the raw amniotic fluid. Typically, the de-cellularized amniotic fluid retains more than 80% of the amniotic proteins compared to the raw amniotic fluid. In some embodiments, D-HAF compositions retain most amniotic factors after short-term or long-term storage under temperature-controlled conditions either as a liquid or as lyophilized powder, for example, at least 50% of the total protein content compared to that of the fresh D-HAF, preferably more than 80%.

The fluid dosages for use with a nebulizer will be from about 0.1 cc to about 10.0 cc. In some embodiments, the dosage for use with a nebulizer is about 0.1 cc, about 0.2 cc, about 0.5 cc, about 1.0 cc, about 2.0 cc, about 3.0 cc, about 5.0 cc, and about 10.0 cc. Generally, volumes used here refer to freshly processed, sterile de-cellularized human amniotic fluid i.e. 1x strength without any dilution or concentration. In some embodiments, the volumes for use with a nebulizer need to be adjusted/increased to match the amount of active ingredients in the amniotic fluid formations, in particular if the formulations were stored for a long period of time where active ingredients (amniotic factors) have deteriorated over time. In some cases where lyophilized amniotic fluid formulations are used, these volumes refer to the volume of fluid when the lyophilized powder is reconstituted with the initial volume of sterile water i.e. 1x strength.

The sterile amniotic fluid formulation can be administered in concentrated form, diluted with sterile water, saline or buffer, preferably in the form of aerosol. It can include additional therapeutic, prophylactic or diagnostic agent, either mixed in with the formulations, or in separate containers to be used in conjunction with, subsequent to, or alternation with treatment with amniotic fluid formulation of the disclosure. The efficacy is determined by physician evaluations, patient self-evaluations, imaging studies and quality of life evaluations.

Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions. D-HAF can be formulated for storage as a fluid or solid (i.e., powder). In preferred embodiments, DHAF is formulated for storage as a liquid (i.e., above freezing temperatures).

1. Solutions, Emulsions and Suspensions

Numerous formulations are known and available. Solutions can be the sterile filtered amniotic fluid, concentrated or diluted with water, buffered saline, or an equivalent. Emulsions are generally dispersions of oily droplets in an aqueous phase. There should be no evidence of breaking or coalescence. Suspensions contain solid particles dispersed in a liquid vehicle; they must be homogeneous when shaken gently and remain sufficiently dispersed to enable the correct dose to be removed from the container. Sediment may occur, but this should disperse readily when the container is shaken, and the size of the dispersed particles should be controlled. The active ingredient and any other suspended material must be reduced to a particle size small enough to be aerosolized and to prevent irritation and damage to the lining of the lungs. They may contain suitable additives, such as antimicrobial agents, antioxidants, and stabilizing agents.

When the solution is dispensed in a multidose container that is to be used over a period of time longer than 24 hours, a preservative must be added to ensure microbiologic safety over the period of use.

Formulations should be prepared depending on the intended use of the D-HAF and are well-known to those skilled in the art.

For example, for pulmonary applications, the pH of the formulations should be ideally equivalent to that of linings of the lung, which may vary depending on the precise location and the severity of the disease. However, the decision to add a buffering agent should be based on stability considerations. The pH selected should be the optimum for both stability of the active pharmaceutical ingredient and physiological tolerance. If a buffer system is used, it must not cause precipitation or deterioration of the active ingredient. The influence on the nebulization should also be taken into account.

Although solutions with a physiological pH are ideal, the surfaces of the lung tolerate a larger range, 3.5 to 10.0. Buffers or pH adjusting agents or vehicles can be added to adjust and stabilize the pH at a desired level. The D-HAF formulations are buffered at the pH of maximum stability of the active ingredient(s) they contain. The buffers are included to minimize any change in pH during the storage life of the drug; this can result from absorbed carbon dioxide from the air or from hydroxyl ions from a glass container. Changes in pH can affect the solubility and stability of the active ingredient(s). Consequently, it is important to minimize fluctuations in pH. The buffer system should be designed sufficient to maintain the pH throughout the expected shelf-life of the product, but with a low buffer capacity so that when the formulation is nebulized and deposited onto the linings of the lungs, the buffer system of the tears will rapidly bring the pH of the solution back to that of the linings. Low concentrations of buffer salts are used to prepare buffers of low buffer capacity.

The preparation of aqueous D-HAF formulations requires careful consideration of the need for isotonicity, a certain buffering capacity, the desired pH, the addition of antimicrobial agents and/or antioxidants, the use of viscosity-increasing agents, and the choice of appropriate packaging. The formulations are considered isotonic when the tonicity is equal to that of a 0.9% solution of sodium chloride. The linings of the lungs can generally tolerate solutions equivalent to 0.5-7.0% of sodium chloride.

Solutions that are isotonic, i.e. an amount equivalent to 0.9% NaCl is ideal for comfort and should be used when possible. There are times when hypertonic solutions are necessary therapeutically, or when the addition of an auxiliary agent required for reasons of stability supersedes the need for isotonicity. A hypotonic solution will require the addition of a substance (tonicity adjusting agent) to attain the proper tonicity range.

In some instances, the formulation is distributed or packaged in a liquid form. Alternatively, formulations for administration can be packed as a solid, obtained, for example by lyophilization of a suitable liquid formulation. The solid can be reconstituted with an appropriate carrier or diluent prior to administration.

Solutions, suspensions, or emulsions for pulmonary administration may be buffered with an effective amount of buffer necessary to maintain a pH suitable for administration. Suitable buffers are well known by those skilled in the art and some examples of useful buffers are acetate, borate, carbonate, citrate, and phosphate buffers.

Solutions, suspensions, or emulsions for pulmonary administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for pulmonary administration may also contain one or more preservatives to prevent bacterial contamination. Suitable preservatives are known in the art, and include polyhexamethylenebiguanidine (PHMB), benzalkonium chloride (BAK), stabilized oxychloro complexes (otherwise known as PURITE®), phenylmercuric acetate, chlorobutanol, sorbic acid, chlorhexidine, benzyl alcohol, parabens, thimerosal, and mixtures thereof.

Solutions, suspensions, or emulsions for pulmonary administration may also contain one or more excipients known art, such as dispersing agents, wetting agents, and suspending agents.

In the preferred embodiments, D-HAF formulations for pulmonary administration do not contain any additives and are packaged in sterile form.

D-HAF formulations containing amniotic factors can be supplied as a clear one-part solution in a suitable container for storage at 4° C., or for storage at −20° C., or at −80° C. For example, liquid formulations in prefilled aliquots can be suitable for storage at 1-5° C., or for storage at −20° C., or at −80° C. The liquid formulation can be suitable for topical application to surfaces of lungs. In other embodiments, the fluid can be supplied as a kit that can be stored at 4° C., at −20° C., or at −80° C. until needed.

D. Kits

In some embodiments, the described compositions are provided in a kit. Typically, the described compositions are prepared using a pharmaceutically acceptable carrier composed of materials that are considered safe and effective and may be administered to an individual without causing undesirable biological side effects or unwanted interactions. Typically the D-HAF composition will be in a single dose unit, for example in an ampoule ready for use with nebulizers. The D-HAF composition is in a single dose unit of about 0.1 cc to about 10.0 cc. In some embodiments, the D-HAF composition is in a single dose unit of about 0.1 cc, about 0.2 cc, about 0.3 cc, about 0.4 cc, about 0.5 cc, about 1.0 cc, about 2.0 cc, about 3.0 cc, about 4.0 cc, about 5.0 cc, about 6.0 cc, about 7.0 cc, about 8.0 cc, about 9.0 cc, or about 10.0 cc.

In some embodiments, the kit includes a first component containing liquid to rehydrate the dry components in a second component. For example, the first component is either water, or saline solution; and the second component is lyophilized D-HAF formulation.

In preferred embodiments, the kit includes instructions to instruct patients or practitioners as to how the dose should be used in conjunction with a nebulizer, such as how to open it and transfer its contents into the nebulizer, how to operate the nebulizer and for how long nebulizing should be continued to complete administration of the dose.

III. Methods of Making

Methods of preparing the sterile de-cellularized human amniotic fluid (D-HAF) formulations are provided. D-HAF contains over 300 human growth factors. D-HAF is devoid of amniotic stem cells and elements of micronized membrane or chorion particles. The purified fluid is sterilized without the use of harsh terminal irradiation, e-beam or Ethylene Oxide (EO). In the preferred embodiment, the process consists of separating the cells from the AF using centrifugation and utilizing a series of filtration devices to remove all remaining cells and bioburden. Each lot is tested for bioburden and is certified sterile to contain <1 harmful organisms. These steps are generally applicable for purifying amniotic fluid from other sources, for example horses, pigs, and buffalos.

A. Preparation

In some embodiments, the formulation is prepared from sterile human amniotic fluid obtained from a pregnant woman. The formulation is free of amniotic membrane particulate matter, i.e. cells, large particles and other undissolvables are removed, preferably by high speed centrifugation to obtain clarified amniotic fluid. The clarified amniotic fluid is then filtered through filters having a pore size of about 5 μm to about 10 μm to obtain a micron filtrate, followed by filtering the micron filtrate through filters with a pore size of about 1.0 μm to obtain a second filtrate, followed by filtering the filtrate through submicron filters with the pore size of 0.45 μm or/and 0.2 μm to obtain the sterilely filtered amniotic fluid.

Those of skill in the art are well-acquainted with methods of safely and humanely obtaining samples of AF, and of the need to maintain sterility of the AF during such procedures. Suitable sources, e.g. of human AF, include AF that is obtained from patients who are undergoing amniocentesis, patients who are undergoing a Cesarean section delivery, and patients undergoing normal delivery using a specially designed receptacle to collect the fluid after rupture of membranes.

In one embodiment, the collection procedure is performed in a sterile operating room environment during an elective C-section. Typically, the woman is undergoing a pre-caesarian surgical method, and the step of obtaining the sterile human amniotic fluid includes the steps of turning on a ultrasound device to provide guidance for the process of obtaining human fluid from the woman, inserting a blunt tip needle into the amniotic sac of the woman, attaching the blunt tip needle to a three-way stopcock, connecting a Luer lock syringe to the three-way stopcock, connecting a first end of a length of sterile tubing with the three-way stopcock, and collecting sterilely the amniotic fluid through the blunt tip needle and sterile tubing into a collection container.

In this embodiment, the sterile collection container includes a pump with a suction device. The suction device is a low suction device or a spring loaded low suction device. The suction device is fluidly connected to an internal balloon. This embodiment further includes manually pumping up the internal balloon in the sterile collection container using the low suction device to allow a low-level suction and collection of the amniotic fluid.

In one embodiment, the AF collected is stored and shipped at 2-8° C. Shipments are made overnight in insulated cooler boxes with ice packs.

In one embodiment, processing is done under sterile conditions, in a Class 100 laminar flow hood in a clean room. As much AF as possible is separated from any solid debris. AF is transferred to sterile 500-2,000 mL containers (size depends on initial volume). Processing is performed at below 25° C. during the process.

In some embodiments, the step of removing cells, large particles and other solids from the human amniotic fluid includes a first step of centrifuging or depth filtering the human amniotic fluid. In some embodiments, the human amniotic fluid is centrifuged at about 5,000 rpm to about 10,000 rpm for about 30 minutes to about 60 minutes. Peristaltic pumps are used to transfer the AF to clean, sterile 250 mL centrifuge bottles without over-filling the bottles. The weight of each bottle should not vary more than 2.0 grams when placed in the rotor. Use the sterile rotor sleeves over the bottles to keep them clean. Spin the bottles at 10,000 rpm for 60 minutes in the Sorvall refrigerated centrifuge. Delicately decant or pump the supernatant to a sterile container and save the pellet material. An optional second centrifugation is used when the AF is not clear of debris after the initial centrifugation. In one embodiment, the AF supernatant from the first centrifugation is transferred to sterile 50 mL centrifuge tubes which are spun at 5,000 rpm for 60 minutes. AF supernatant is decanted into a sterile container and any significant pellet volume saved.

In some embodiments, the AF supernatant is subsequently subject to a series of filtration steps. In one embodiment about 5 μm to about 10 μm filters are used for the first filtration (pre-filtration) are cellulose ester filters, glass fiber filters, nylon capsule filters or nylon cartridge filters. In some embodiments, multiple pre-filters are used, depending on the clarity of the filtered solution. The filters with the pore size of 1.0 μm (Filtration 1.0 u) are capsule filters or cartridge filters. The filters with the pore size of 1.0 μm are poly ether sulfone, poly vinylidene fluoride or cellulose acetate membrane filters. Final filtration is carried out using filters with the pore size of 0.45 μm or 0.2 μm which are capsule filters or cartridge filters. The filters with the pore size of 0.45 μm or 0.2 μm are poly ether sulfone membrane filters, poly vinylidene fluoride or cellulose acetate membrane filters.

In some embodiments, the sterilely filtered human amniotic fluid contains growth factors including human growth hormone, transforming growth factor beta 1, vascular endothelial growth factor, epidermal growth factor, transforming growth factor beta 3, and growth differentiation factor 11 or combinations thereof.

In some embodiments, the sterile amniotic fluid further includes the step of filling and packaging. For example, sterile D-HAF is filled in syringes ready for application. Each shot should weigh 0.90-1.10 grams. Recalibrate pump settings if needed. Begin the fill operation using the nests of 100 Schott TopPac 1 mL syringes. Purge the air 3× from the Impro stoppering system. Stopper each nest immediately after filling using the Impro vacuum stoppering system connected to 0.2 μm filtered air. Aseptically perform at least (3) particulate counts and open media controls over the course of the run.

In a further embodiment, the filled syringes are capped with a sterile plunger. Place the syringe in a Mangar mylar pre-labeled pouch with the plunger rod towards the chevron side of the pouch. Seal the pouch with a heat sealer set to 270° F., 2.4 second dwell, 170° F. cooling temperature. Visually inspect the seals after sealing. Note that the intact syringe constitutes the primary sterile barrier of the AF product.

In yet another embodiment, the AF fluid is filled in sterile 2 cc vials with stoppers and 13 mm crimp caps as a barrier.

In some embodiments, the sterile amniotic fluid further includes the step of lyophilizing the sterile amniotic fluid to obtain a lyophilisate thereof. The method further includes irradiating the lyophilisate by e-beam irradiation or gamma ray irradiation to reinforce the sterility.

In some embodiments, the amniotic fluid from the final filtration is aseptically transferred to syringes or vials, and kept in a deep freezer at about −80° C. to about −20° C. for long term storage. The sterile amniotic fluid is dried in the vial via lyophilization in a built-in a sterile environment. The lyophilisate derived from the amniotic fluid is reconstituted with sterile water before injection or topical administration. The lyophilisate can be stored at from +4° C. to about +25° C. (room temperature).

In some embodiments, the lyophilisate derived from amniotic fluid through lyophilization may be irradiated by e-beam irradiation or gamma ray irradiation to add another guarantee for the final sterility of the powder. Irradiation of a lyophilisate is much less denaturing for proteins and peptides than irradiating aqueous solutions, because the absence of water considerably reduces the production of reactive superoxide anions and their diffusion during irradiation. Such superoxide anions are the main cause of splitting peptide bonds and chemically modifying amino acids of protein and peptides. After lyophilization, the amniotic fluid is reconstituted by adding the initial volume of water. After gentle homogenization, the powder is quickly dissolved in about one minute.

The reconstituted amniotic liquid is transparent and may be used for wound healing, cosmetic, orthopedic, ophthalmic, or pulmonary applications in particular for asthma and COPD patients.

In some embodiments, tools to obtain sterilely filtered human amniotic fluid from a woman, include a three-way stopcock, a sterile blunt tip needle aseptically attached to the three-way stopcock, a Luer lock syringe aseptically connected to the three-way stopcock, a sterile tubing aseptically connected to the three-way stopcock, a collection container or a collection container including a pump with suction device connected with the sterile tubing, a set of filters having the pore size of about 5 μm to about 10 μm, a set of capsule or cartridge filters having the pore size of about 1 μm, a set of capsule or cartridge filters having the pore size of about 0.45 μm or 0.2 μm, a set of sterile syringes or vials to store the sterile filtered amniotic fluid and operating instructions on using the kit to obtain sterilely filtered human amniotic fluid. The filters having the pore size of from about 5 μm to about 10 μm and the capsule or cartridge filters are made from cellulose ester, glass fiber or nylon.

The sterile collection container may include a pump with a suction device. In one aspect of this embodiment suction device may be a low suction device or spring loaded low suction device. In another aspect the suction device may be fluidly connected to an internal balloon. Further to this aspect the method includes manually pumping up the internal balloon in the sterile collection container using the low suction device to allow a low-level suction and collection of the amniotic fluid. In yet another aspect the sterile collection container may include an inlet. Further to this particular aspect the method includes connecting a second end of the tubing to the inlet of the sterile collection container. The sterile collection container may include a vent having a cap.

In some embodiments, utilizing the incision site immediately prior to performing the C-section and with ultrasound guidance to protect the fetus and mother provides a minimal or no risk environment for collection. Collection is achieved via a low level suction established within a collection container and/or via gravity. Typically, high speed centrifugation filtration with 5 to 10 μm filters (low protein binding filter) is used to complete the removal of cells and large particles. Submicron filtration would then be conducted with 1 μm and 0.45 μm or/and 0.2 μm filters (low protein binding filter), two in a series connection, to remove gross contaminates. Under this condition, soluble growth factors will pass through this filter to achieve a semi-sterile condition, very low bioburden counts. If under a strict aseptic operation condition, a $10^{-3}$ sterility assurance level is achieved. A $10^{-6}$ sterility assurance level can be achieved by submicron filtration with a 0.22 µm filter (low protein binding filter) at the end and sterile packaging to achieve a sterile product. One would monitor the filtrate after each filtration step to determine which components were removed and then to determine which process to use to achieve the desirable product.

One may use membrane filters including or made of hydrophilic polyethersulphone (PES) to filter protein solutions. Filter disks for small volumes and different sizes of cartridges for larger volumes such 1 litre and more. Hydrophobic membranes like PTFE which are designed for liquids devoid of proteins should not be used. Start with centrifugation at 5000 to 8000 rpm for at least 30 minutes. Next, the supernatant is filtered with a prefilter to remove residual protein aggregates and precipitates in suspension (AP20 can be used). If one directly uses a 0.6/0.2 µm filter, after prefiltration, one may experience slow filtration rates and the flow may stop too quickly. It may be desirable to make intermediate filtration steps using 1.2 µm and 0.8 µm membranes. In one embodiment, a final filtration through 0.2 µm is necessary to get the best sterility assurance level and produce a sterile amniotic fluid for injections.

B. Storage

The final filtrate can be stored in frozen condition at about −20° C. to about −80° C. for long-term storage. In addition, the sterilely filtered amniotic fluid may be distributed in vials equipped with special rubber stoppers for sterile lyophilization.

The lyophilization is carried out in a sterile environment. The rubber stoppers on the vials are then automatically pushed down in the freeze dryer to definitively close them. Then an aluminum cap is sealed on each vial to protect its sterile content. In such a lyophilized state, the amniotic fluid may be stored at +4° C. or room temperature for at least one year without decrease of its biological activity. For its medical use, the sterile amniotic fluid may be reconstituted by adding the initial volume of sterile water to the powder in order to restore a transparent and homogeneous physiological liquid.

The decellularization and purification process protects the growth factors and other biological components of amniotic fluid from chemical and enzymatic degradation. Molecules contained within the fluid are stabilized against degradation, avoiding the need for chemical or physical modification to maintain the biological activity of the molecules over extended periods of time. Therefore, D-HAF prepared according to the described methods can be stored for long periods of time, allowing for a broad range of application methods, including distribution and storage as aerosols, solutions, powders, etc.

In some embodiments, the sterile D-HAF is refrigerated at about 1° C. to about 10° C. for long-term storage. In a further embodiment, the sterile D-HAF is refrigerated at 4° C. for up to 12 months and more. For example, fluids purified according to the described methods retain the biological properties of the component molecules over extended periods of storage, ideally without the need for freeze/thawing.

Preferably, the long-term storage does not reduce the quantity of the total soluble proteins or factors present in the D-HAF. For some embodiments, the total soluble proteins retained after long-term storage in refrigerated conditions is about 10%, 20%, 30%, 40%, 50%, 60%, 70%, 80%, or 90% of the fresh D-HAF.

The protein quantities remaining soluble in the D-HAF after a period of storage is assessed by common protein quantification methods such as bicinchoninic acid (BCA) assay, Bradford assay, Lowry assay, and ultraviolet absorption (at 280 nm). To quantify individual proteins, high-throughput methods such as high-density screening arrays (RayBiotech, Norcross Ga.) are used.

Storage does not reduce, prevent or otherwise alter the biological activity of any one or more of the amniotic factors of the DHAF. For example, in some embodiments, the biological activity of one or more amniotic factors is retained throughout storage for extended periods of time. The activity of any one or more of the amniotic growth factors of the stored product can be assessed as a % compared to that of the fresh (raw) product, or compared to the D-HAF prior to storage. Therefore, in some embodiments, little or no statistically significant changes in the biological activity of the amniotic factors are observed when using D-HAF stored at 4° C. for up to a day, 2 days, 3 days, 4 days, 5 days, 6 days, up to one week, up to 2 weeks, up to 3 weeks, up to 4 weeks, up to one month, up to 2 months, up to 3 months, up to 4 months, up to 5 months, up to 6 months or more than 6 months. In other embodiments, the activity of any one of the proteins in the amniotic fluid are reduced by 50%, 40%, 30%, 20%, 10%, 5%, or less than 5% relative to the raw amniotic fluid prior to the de-cellularizing process.

In some embodiments, one or more of the growth factors is reduced after storage. For example, such growth factors include FGF7, MMP-9, GCSF, MMP-7, MMP-13, TGF-β, FGF-4, EG-VEGF and IL-8. In other embodiments, one or more of the growth factors is reduced after freeze/thawing. For example, such growth factors include FGF-21, ANG2, GDNF, FGF-19, TIMP-2, ANG-1, TGFβ1 and M-CSF. In a preferred embodiment, one or more of the growth factors is increase compared to the fresh D-HAF, presumably due to enhanced stability at these storage conditions. Some exemplary growth factors include VEGF-α, TNF-α, and HGF. In a further embodiment, variable changes in the growth factors such as angiotensinogen, PDGF-AA, TGF-α, EGF and SCF.

In some embodiments, inflammatory markers are decreased after refrigeration at 2-8° C. for one, two, three or four weeks. For example, the amount of one or more of the inflammatory proteins present in the refrigerated sample is reduced by about 1%, 5%, 10%, 20%, 30%, 40%, 50%, 60% 70%, or 80% compared to that of the fresh (raw) product. Some exemplary inflammatory markers include Eotaxin-2, IL-6, CCL18, total GRO, CXCL5, 6Ckine, and MIP-3a.

In some embodiments, inflammatory proteins are decreased after freezing. For example, the amount of one or more of the inflammatory proteins present in the sample stored in frozen condition at about −20° C. to about −80° C. is reduced by about 5%, 10%, 20%, 30%, 40%, 50%, 60% 70%, 80% or 90% compared to that of the fresh (raw) product. Some exemplary inflammatory markers include IL-la, CXCL9, MIP-1α, and CCL5.

In other embodiments, inflammatory markers are increased after being stored for long-term either in refrigerated or frozen conditions. Some exemplary inflammatory markers include TNF-α, MIP-1β, and MCP-2.

In a preferred embodiment, anti-inflammatory molecules are not significantly decreased after being stored refrigerated or frozen for one or more days, weeks or months. In another embodiment, one or more of the anti-inflammatory molecules is decreased in D-HAF following a period of refrigeration. Some exemplary anti-inflammatory molecules include IL-8, IL-13, IL-27, CTLA-4, and IL-21. In another embodiment, one or more of the anti-inflammatory molecules is decreased in the D-HAF stored in frozen conditions. Some exemplary anti-inflammatory molecules include IL-1Ra and TGFβ1.

IV. Methods of Use

The amniotic fluid formulations may be administered alone or in any appropriate pharmaceutical carrier, such as a liquid, for example water, and saline, or a powder, for administration to the respiratory system. The formulations can be delivered by any method and/or device which is currently used for pulmonary delivery. For example, nebulizers, aerosolizers and inhalers can be used.

Aerosol dosage, formulations and delivery systems may be selected for a particular therapeutic application, as described, for example in Gonda, I. "Aerosols for delivery of therapeutic and diagnostic agents to the respiratory tract," in Critical Reviews in Therapeutic Drug Carrier Systems, 6:273-313 (1990), and in Moren, "Aerosol dosage forms and formulations," in Aerosols in Medicine. Principles, Diagnosis and Therapy, Moren, et al., Eds., Esevier, Amsterdam, 1985, the disclosures of which are incorporated herein by reference.

A. Methods of Treatment

The amniotic fluid formulations are provided as a medicament for improving exercise tolerance, improving the endurance time, reducing the intensity of breathing discomfort, and/or increasing the exercise capacity in patients with any pulmonary disorders.

In some embodiments, the amniotic fluid formulations, generally with a pharmaceutically carrier are for use as a medicament for a treatment to improve exercise tolerance and/or endurance time in patients with lung disorders. Accordingly, in one aspect, the amniotic fluid formulations are provided as a medicament for improving exercise tolerance in a patient with COPD, or asthma comprising administering to the patient a therapeutically effective amount of D-HAF formulations. In some embodiments, the amniotic fluid formulations are provided as a medicament for reducing the intensity of breathing discomfort in a patient with COPD, or asthma whilst exercising comprising administering to the patient a therapeutically effective amount of D-HAF formulations.

In some embodiments, the amniotic fluid formulations result in increase in exercise duration. For example, if a patient could perform exercises for a maximal duration of 5 minutes prior to the treatment with D-HAF, the treatment with the disclosed formulations may help to extend that interval to about 6 min, 7 min, 8 min, or more than 8 min. Generally, the improvement in exercise tolerance is observed within days, weeks, or months after the initial treatment, and exercise duration is extended up to 10%, 20%, 30%, 40%, 50%, 60%, 70%, 80%, 90%, 100%, 200%, 300%, 400%, 500% or more than 500%.

The amniotic fluid formulations are provided as a medicament for improving baseline blood oxygen saturation, and/or reducing local inflammation in the lung of patients with any pulmonary disorders.

In some embodiments, the amniotic fluid formulations result in increase in baseline blood oxygen saturation by 5%, 10%, 20%, 30%, 40%, 50%, or more than 50% in the absence of any external oxygen therapy.

In some embodiments, the amniotic fluid formulations result in reduction in inflammation in the lungs. These can be measured by systemic inflammation markers such as measuring the plasma levels of C-reactive protein (CRP), soluble tumour necrosis factor receptor (sTNFR)-1, osteoprotegrin, neutrophil activating peptide-2, CXCL16 and monocyte chemoattractant protein-4. Alternatively, it is measured by a ventilation/perfusion lung scan (a V/Q lung scan).

1. Disorders and Diseases to be Treated

The formulations can be used for various lung disorders, including, but not limited to, any obstructive lung disorders, and restrictive lung disorders. In some embodiments, the disclosed formulations are effective in improving exercise endurance, increasing in baseline blood oxygen saturation, and/or reducing inflammation in the lungs of patients with any obstructive lung disorders, and restrictive lung disorders. In some embodiments, the disclosed formulations are effective in helping patients to be less dependent on using other supplemental treatment such as bronchodilators, and/or oxygen therapy.

The formulations are particularly suited for treatment of COPD and asthma, including, but not limited to, bronchitis, chronic bronchitis, emphysema, and associated cor pulmonale (heart disease secondary to disease of the lungs and respiratory system) with pulmonary hypertension, right ventricular hypertrophy and right heart failure, bronchial asthma, allergic asthma and intrinsic asthma, e.g., late asthma and airway hyper-responsiveness.

Other non-limiting examples include bronchiectasis, interstitial lung disease, and alpha-1 antitrypsin emphysema.

Acute respiratory distress syndrome (ARDS) is a rapidly progressive disease occurring in critically ill patients. The main complication in ARDS is that fluid leaks into the lungs making breathing difficult or impossible. ARDS may initially be diagnosed as pneumonia or pulmonary edema (fluid in the lungs from heart disease). Patients with ARDS have shortness of breath, often severe. They also have a cough and many have fever. Those with ARDS also have fast heart rates and rapid breathing. Occasionally, they experience chest pain, especially during inhalation. Some patients who have very low oxygen levels may have bluish coloring of nails and lips from the severely decreased oxygen levels in the blood. Thus, in some embodiments, the disclosed formulations are used for treating, alleviating, or preventing one or more symptoms associated with acute respiratory distress syndrome.

Intensive care unit (ICU) syndrome, or ICU psychosis occurs in Patients who become psychotic in intensive care units, with underlying causes such as anxiety, sleep deprivation, sensory deprivation and overload, immobilization, an unfamiliar environment and pain. Thus, in some embodiments, the disclosed formulations are used for treating, alleviating, or preventing one or more pulmonary symptoms associated with Intensive care unit (ICU) syndrome.

Systemic inflammatory response syndrome (SIRS), sepsis, severe sepsis, septic shock, and multiple organ dysfunction syndrome (MODS) are common risk factors for the development of acute lung injury in patients. Thus, in some embodiments, the disclosed formulations are used for treating, alleviating, or preventing one or more symptoms associated with Systemic inflammatory response syndrome (SIRS), sepsis, severe sepsis, septic shock, or multiple organ dysfunction syndrome (MODS).

Cystic Fibrosis (CF) is an inherited disease that causes thickened mucus to form in the lungs, pancreas and other organs. In the lungs, this mucus blocks the airways, causing lung damage and making it hard to breathe. Thus, in some embodiments, the disclosed formulations are used for treating, alleviating, or preventing one or more symptoms associated with cystic fibrosis.

Pneumonia is a common lung infection caused by bacteria, a virus, fungi or chemicals. It's commonly a complication of a respiratory infection—especially the flu—but there are more than 30 different causes of the illness. Older adults, children and people with chronic disease, including COPD and asthma, are at high risk for pneumonia. Pneumonia symptoms can vary from mild to severe, depending on the type of pneumonia you have, your age and health. The most common symptoms of pneumonia are cough (with some pneumonias you may cough up greenish or yellow mucus, or even bloody mucus), fever, which may be mild or high, shaking chills, shortness of breath, which may only occur when you climb stairs. In some embodiments, the disclosed formulations are used for treating, alleviating, or preventing one or more symptoms associated with pneumonia.

Sarcoidosis is a disease that causes your immune system to overreact, which can lead to health issues. It can cause lung damage, skin rashes, and eye disease and can affect other organs of the body. Many patients with sarcoidosis experience lung problems, which may include persistent dry cough, shortness of breath, wheezing, and/or chest pain. In some embodiments, the disclosed formulations and the methods of use thereof are suitable for managing symptoms associated sarcoidosis in patients.

Idiopathic pulmonary fibrosis (IPF) is a chronic lung disorder characterized by thickening, stiffening and scarring (fibrosis) of tissue within the lungs. Affected individuals develop shortness of breath and progressive lung disease. Ultimately, IPF results in life-threatening complications such as respiratory failure. In some embodiments, the disclosed formulations and the methods of use thereof are suitable for managing idiopathic pulmonary fibrosis in patients. In some embodiments, the disclosed formulations are used for treating, alleviating, or preventing one or more symptoms associated with idiopathic pulmonary fibrosis. In some embodiments, the disclosed formulations are used for reducing, or preventing pulmonary scarring in patients with IPF.

i. Acute Inhalation Injury

The formulations disclosed are suitable for treatment of acute inhalation injury. Inhaled substances may cause injury in pulmonary epithelium at various levels of respiratory tract, leading from simple symptoms to severe disease. Chemical irritants, asphyxiants, toxic metals, products of fires and combustion, and many other substances have been reported to cause acute inhalation injury (Gorguner M et al., *Eurasian J Med.* 42(1): 28-35(2010)). Some cases of acute inhalation injury may involve more than one substance or mechanism. In some embodiments, the disclosed formulations are used for treating, alleviating, or preventing one or more symptoms associated with an acute inhalation injury.

In some embodiments, the disclosed formulations are used for people who are at increased risk of exposing to toxic agents as a prophylactic measure. Some exemplary high-risk individuals are farmers who work near silos, firefighters, coal miners after firing of explosives, welders who work with acetylene torches in confined spaces, military personnel, hockey rink workers, and chemical workers who may be exposed to byproduct fumes in the manufacture of dyes and lacquers constitute some of the occupations at risk. For example, the disclosed formulations are suitable for treating, alleviating, or preventing one or more symptoms of coalworker's pneumoconiosis.

In some embodiments, the disclosed formulations are used for farmers who are at risk of exposing to dust, particulates for example from harvesting hay, crops, pesticides, herbicides, defoliates, and fungicides such as methyl oxide. Other potential toxic agents include fruit ripening gas such as ethylene, carbon dioxide which inhibits growth of micro-organisms, nitrogen as inert filler, and gas mixtures to preserve fresh appearance of fruits, vegetables and meats e.g., 1-methylcyclopropene.

Some further chemical agents that can cause pulmonary injuries include defoliant, ecocide, harassing agent, herbicide, pesticide, nerve agent, and antipersonnel agents. For example, Agent Orange used during the Vietnam war is a blend of two herbicides known as 2,4-D and 2,4,5-T. Two other herbicides, picloram and cacodylic acid, were also used, but in much smaller amounts. In some embodiments, the disclosed formulations are used for treating, and/or alleviating one or more symptoms in subjects with long-term pulmonary injuries due to exposure to agents such as Agent Orange.

Inhalation of a number of gases, mists, aerosols, fumes or dusts may cause irritant lung injury, asphyxiation, or other systemic effects. The use of industrial chemicals with potential toxicity has been on the rise. Accidental spills, explosions, and fires can result in complex exposures to such substances. According to the National Occupational Exposure Survey (NOES 1981-1983), more than one million workers in US are estimated to be under the risk of exposure to respiratory irritants annually; however, data from poison control centers suggest that inhalation injuries occur more frequently in the home environment than in the workplace. The number of people affected varies depending on the environment and may be as high as tens of millions in case of air pollution reaching hazardous levels, for example, due to ozone depletion.

Handling chemicals, working in inadequately ventilated areas, or entering areas of exposure with improper or no protective equipment are generally the reasons for occupational injuries (White S R et al., Emergency medicine: a comprehensive study guide. 6th ed. New York: The Mc Graw Hill Companies, Inc.; 2004). In general environment, random exposures may occur such as mixing household chemicals by mistake, for example bleach and hydrochloric acid mixture, or a gas leak at home, for example carbon monoxide, or smoke containing irritant chemicals, for example pyrolysis products made of synthetic materials when used during a house-fired. Chemicals are used in manufacturing of polyurethane foam, molding, insulation, synthetic rubber, and packaging materials and can induce lung cell injury when inhaled. Chemical toxins and chemical warfare agents, such as tabun, sarin, soman, cyclosarin, VX nerve gas, sulfur mustard, Agent Orange, chlorine, phosgene, and diphosgene, can cause life-threatening lung disease (Kales S N et al., *N Engl J Med.* 19; 350(8):800-8 (2004); Newman L S et al., *N Engl J Med.* 26; 333(17): 1128-34 (1995)).

a. Common Chemical Irritants

Chemical irritants in occupational and environmental areas are usually the cause of acute inhalation toxicity. Exemplary chemical irritants include chlorine, hydrogen chloride, ammonia, hydrogen fluoride (HF) and hydrofluoric acid, sulphur dioxide ($SO_2$), nitrogen oxides, phosgene, hydrogen sulfide ($H2S$). In some embodiments, the disclosed formulations are used for treating, alleviating, or preventing one or more symptoms associated with an acute inhalation injury caused by chemical irritants.

b. Asphyxiants

In some embodiments, the disclosed formulations are used for treating, alleviating, or preventing one or more symptoms associated with an acute inhalation injury caused by one or more asphyxiants. Unlike chemical irritants, asphyxiant has a different mechanism. However, some asphyxiants such as hydrogen sulfide may also have a chemical irritation effect. Based on their effects, asphyxiants can be divided into two groups: simple asphyxiants which act by displacing oxygen from inspired air resulting in a reduced fraction of inspired oxygen and subsequent hypoxemia, and chemical asphyxiants, such as carbon monoxide and hydrogen cyanide, which act by interfering with oxygen delivery or utilization. However, any gas in high concentration can act as an asphyxiant. Although, for example, methane, ethane, argon, and helium are more innocent at low concentrations, at high exposure levels they can displace oxygen or block the reaction of cytochrome oxidase or hemoglobin, impairing cellular respiratory and oxygen transport.

c. Burns and Smoke

In some embodiments, the disclosed formulations are used for treating, alleviating, or preventing one or more symptoms associated with an acute inhalation injury caused by burns and/or smoke inhalation. Exposure to heat, particulate matter, and toxic gases are considered the exposure to smoke. Closed-space fires and conditions that cause unconsciousness are often the reason for inhalation injuries. Between 20% and 30% of burn victims suffer from pulmonary complications, with an incidence rate correlating with the severity of the burn and a history of being in enclosed space. Tracheobronchial damage and pulmonary complications, which are common and an important cause of morbidity and mortality, may be accompanied by infection, shock, and the consequences of therapy, including overhydration. The improvements in the treatment of burn shock and sepsis has rendered inhalation injury the main cause of mortality in the burn patients (Hartzell G E, Toxicology. 115(1-3):7-23(1996)).

"Smoke inhalation" is a generic term that refers to a potential exposure to a wide variety of substances because of the complex chemistry of heat decomposition and pyrolysis. Both firefighters (both urban and wildland) and non-occupational victims can be exposed to substantial numbers of irritants. Thermal injuries typically limited to upper airways; however, those below the vocal cords occur only with steam inhalation. The entire respiratory tract can be affected by smoke inhalation from fires. Smoke contains particulate matter which is formed from incomplete combustion of an organic material, usually less than 0.5 µm in size. Thus, small particles can easily reach the terminal bronchioles and here they can initiate an inflammatory reaction, leading to bronchospasm (Ainslie G, Respir Med. 87(3):169-74 (1993)).

d. Chemical Warfare and Riot Control Agents

In some embodiments, the disclosed formulations are used for treating, alleviating, or preventing one or more symptoms associated with a pulmonary injury caused by chemical warfare and/or riot control agents. Chemical Warfare and Riot Control Agents of the past, especially during World War I and II, were gases such as Agent Orange, mustard gas, phosgene and chloropicrin. Today, chemical warfare armamentarium includes systemic toxins derived from organophosphate pesticides. Besides being highly lethal neurotoxins, they also have important respiratory effects, such as bronchorrhea and bronchospasm, which occur via muscarinic receptor stimulation. Riot control agents (crowd control agents, tear gases) aim to incapacitate persons via immediate mucous membrane irritation. Chloroacetophenone and orthochlorobenzamalonitrile are the most common agents worldwide. They have been reported to have mucous membrane effects as well as causing lower respiratory injury. Contrary to tear gases, zinc chloride, which is the primary component of smoke bombs, is a potent lower respiratory tract irritant and may cause severe pulmonary edema. In some embodiments, the disclosed formulations are used to treat, alleviate, or prevent pulmonary edema.

Thus, in some embodiments, the disclosed formulations are used immediately after exposure to any potentially toxic agents to prevent the onset of any pulmonary injuries, and/or to alleviate immediate onset of pulmonary conditions whilst preventing one or more secondary symptoms. In some embodiments, the disclosed formulations are used to treat, alleviate, or prevent any pulmonary tissue scarring. In some embodiments, the disclosed formulations are used to treat veterans who exposed to toxic gas such as Agent Orange, mustard gas during the wars in managing their pulmonary health.

e. Toxic Metals

In some embodiments, the disclosed formulations are used for treating, alleviating, or preventing one or more symptoms associated with a pulmonary injury caused by toxic metals. Cadmium and mercury are the most common metals causing inhalation injury. Welding, brazing, or flame cutting metal under poor ventilation are the typical conditions for cadmium exposure typically, while heated metal reclamation processes involve potential mercury exposure risks. Metals or their compounds such as antimony, manganese, beryllium, vanadium and tributyltin rarely cause inhalation injury through the inhalation of fumes or vapors of the certain metals, acute pneumonitis may develop. Heavy metal pneumonitis has been accounted for by the inhibition of enzymatic and other critical cellular functions. In such cases, chelation treatment may be considered (Nemery B, *Eur Respir J.* 3(2):202-19 (1990)).

f. Inhalation Fevers

In some embodiments, the disclosed formulations are used for treating subjects with inhalation fevers prior to any confirmed lung injuries for preventative uses. Inhalation fever includes metal fume fever, polymer fume fever, and organic dust toxic syndrome, all of which share similar clinical findings and prognosis. Exposure to zinc fume and sometimes to copper and magnesium fume causes metal fume fever. Exposure to heated fluoropolymers and high amounts of endotoxin leads to polymer fume fever and organic dust toxic syndrome, respectively, which are characterized with chills, fever, malaise, and myalgia with onset 4 to 8 hours after intense inhalation of fumes or dust. Common respiratory complaints include cough or mild dyspnea.

g. Blast Injury

Lung injury is frequently a component of the polytrauma sustained by military personnel surviving blast on the battlefield. Injuries from explosions arise in a number of ways. In temporal order these include tissue damage from; the blast shock wave (primary blast injury), material propelled into the casualty (secondary), the casualty propelled against other objects (tertiary), heat, chemicals and toxins delivered by the device (quaternary) and finally the systemic inflammatory response provoked in the host (quinary). Fatal blast lung injury (BLI) can be sustained in the absence of any other external signs of trauma, thoracic or otherwise. The clinical diagnosis of blast lung is based on context, clinical symptoms and radiology. Symptoms may include respiratory distress, restlessness, and in some cases haemoptysis, associated with cyanosis and hypoxaemia. In some patients symptoms may be significantly delayed. Typical findings described to date include unilateral or bilateral focal opacities, diffuse unilateral or bilateral loss of lung translucency which, if unilateral, may be associated with reduced rib-expansion, and radiological evidence of barotrauma. The latter may include pneumothorax, pneumomediastinum, pneumopericardium, surgical emphysema, interstitial emphysema and haemothorax secondary to pulmonary parenchymal lacerations.

In some embodiments, the disclosed formulations are used for treating, alleviating, or preventing one or more symptoms associated with a pulmonary condition associated with blast injury. In some embodiments, the disclosed formulations are administered to anyone with pulmonary blast-related injuries, or anyone suspected to have exposed to blast injury, within the "Golden Hour" following impact. In some embodiments, the disclosed formulations are administered to anyone who is susceptible to pulmonary blast-related injuries to prevent onset of any symptoms, or to prevent one or more secondary complications associated with the lung. In some embodiments, the disclosed formulations are administered in combination with one or more further interventions such as supplemental oxygen.

h. Complex Exposures

In some embodiments, the disclosed formulations are used for treating, alleviating, or preventing one or more symptoms associated with a pulmonary injury caused by exposure to one or more toxic compounds. Individuals who suffer inhalation injuries are frequently exposed to complex mixtures of toxic compounds, not just a single agent. Though poorly characterized, such mixtures may contain admixtures of combustion products, pyrolysis products, metals, particulates, and gas. Such mixtures have been shown to have the potential to produce a range of airway and diffuse interstitial lung lesions.

Individuals who are accidentally exposed to toxic gases usually recover completely. However, sometimes acute life threatening or chronic severe complications may develop. Thus, in some embodiments, the disclosed formulations are used for preventing one or more symptoms of secondary/chronic pulmonary complications in patients who have had acute inhalation injuries. In some embodiments, the disclosed formulations are used for treating, alleviating one or more symptoms of patients who have had acute inhalation injuries and developed chronic pulmonary complications. Some exemplary chronic pulmonary complications include reactive airway disease syndrome (RADS), bronchiolitis obliterans (BO, also known as constrictive bronchiolitis), cryptogenic organizing pneumonia (COP), and bronchiectasis.

2. Treating Pulmonary Conditions in Animals

The formulations disclosed may be administered to mammalian subjects, including but not limited to humans, primates such as monkeys and apes, canines such as dogs, felines such as cats, bovines such as cows, equines such as horses, swine such as pigs, and rodents such as mice and rats.

The compositions and methods of managing or treating a pulmonary disease in equines, preferably horses, are described. In some embodiments, the horses in need of treatment are racehorses. Common phenotypic manifestations of airway diseases in horses include coughing, nasal discharge, increased respiratory effort and poor performance or exercise intolerance. Additionally, fever, depression, decreased appetite and weight loss can be observed in infectious airway diseases (Couetil et al, 2007 and Kutasi et al, 2011). In some embodiments, the pulmonary diseases in need of treatment are inflammatory airway diseases, or reactive airway disease (heaves). In some embodiments, the pulmonary disease in need of treatment is recurrent airway obstruction (RAO), or formally known as chronic obstructive pulmonary disease (COPD). In some embodiments, the disclosed formulations are administered using equine inhalers for enhanced delivery.

Exercise-induced pulmonary hemorrhage (EIPH) is seen in most racehorses and in many other horses used in equine sports (e.g., polo, barrel racing, 3-day events) that require strenuous exercise for short periods of time. Epistaxis is seen in a small proportion (~5%) of horses with EIPH. Blood in the tracheobronchial tree is identified in 45%-75% of racehorses via endoscopic examination, and hemorrhage is detected by cytologic examination of bronchoalveolar lavage in >90% of racehorses. EIPH is common in horses undertaking intense exercise, but it has also been reported in human athletes, racing camels and racing greyhounds. Thus in some embodiments, The formulations disclosed are suitable for treating, alleviating, or preventing one or more symptoms associated with exercise induced pulmonary hemorrhage (EIPH) in mammals, especially in racing horses. In some embodiments, the formulations disclosed are suitable for treating, alleviating, or preventing one or more symptoms associated with epistaxis.

Other respiratory diseases that are suitable for treatment using the disclosed formulations include viral respiratory infections such as equine herpesvirus infection, equine influenza, equine viral arteritis, and Hendra virus infection; secondary bacterial respiratory infections such as those caused by *Streptococcus equi zooepidemicus, Actinobacillus equuli, Bordetella bronchiseptica, Escherichia coli, Pasteurella* spp, *Pseudomonas aeruginosa*, or *S equi equi*. Secondary bacterial disease may result in mucosal bacterial infections (rhinitis and tracheitis) or may produce more serious invasive disease such as pneumonia and pleuropneumonia. In some embodiments, the formulations disclosed are suitable for treating, alleviating, or preventing one or more symptoms associated with rhinitis, tracheitis, pneumonia, or pleuropneumonia.

The compositions and methods of managing or treating a pulmonary disease in dogs and cats, are also disclosed. Pulmonary diseases in dogs/cats include but not limited to obstructive and allergic lung diseases such as asthma, bronchitis, or bronchial asthma. In some embodiments, the pulmonary disease in need of treatment is COPD. In its early stages in dogs/cats, the main symptom of COPD is chronic coughing, or coughing that persists for longer than a month. The cough is usually 'dry' or harsh, and gagging is common after coughing. As the disease progresses, the dogs/cats may have difficulty breathing and often has decreased exercise tolerance (tires easily) or may even faint with overexertion. Breathing may become noisy, and the animal may wheeze when exhaling. In later stages, the gums may develop a bluish tinge as a result of lack of oxygen. Dogs/Cats with COPD rarely have a fever and usually their appetite remains normal. In some embodiments, the disclosed formulations are administered using inhalers specifically designed for the animals for enhanced delivery.

The compositions and methods of treating, alleviating, or preventing a pulmonary injury in animals having exposed to toxic substances, or having acute inhalation injuries, are also disclosed. Chemical irritants, asphyxiants, toxic metals, products of fires and combustion or many other agents discussed above can also cause acute inhalation injury in animals.

B. Methods of Administration

The compositions provided are used for treating, preventing, or ameliorating one or more symptoms of a bronchoconstrictive disorder or disease in a subject. Generally, it is not restricted to any specific mode of administration as long as the compositions are deposited at desired sites of treatment. In preferred embodiments, the methods involve administering to the subject via a pulmonary, oropharyngeal, nasopharyngeal, or hypopharyngeal route. In one embodiment, the method includes nebulizer administration to a subject of an effective amount of a composition containing D-HAF, whereby the disease or disorder is treated, or prevented.

1. Nebulizers

The formulations of the present invention are designed for administration by nebulizer. A nebulized solution is one dispersed in air to form an aerosol, and a nebulizer generates very fine liquid droplets suitable for inhalation into the lung. Nebulizers typically use compressed air, ultrasonic waves, or a vibrating mesh to create a mist of the droplets and may also have a baffle to remove larger droplets from the mist by impaction. A variety of nebulizers are available for this purpose, such as ultrasonic nebulizers, jet nebulizers and breath-actuated nebulizers. In preferred embodiments, mouthpieces or masks are typically attached to a patient to aid delivery of the nebulized solution.

The deposition of inhaled medication into the lung and airways is influenced by multiple factors, including the characteristics of the nebulizer device, the formulation properties of the aerosol, the patient's breathing pattern, airway geometry, and potential differences in regional airway ventilation. Differences among nebulizer systems can impact by several-fold the efficiency of drug delivery to the lung. Nebulizers are therefore selected to efficiently deliver the desired amount of formulations to the targeted areas of the lung, with minimized drug-related adverse effects.

One important consideration in choosing an appropriate nebulizer is its ability to generate appropriate droplet size of the aerosol for pulmonary treatment. Generally, small droplet sizes are preferred for more efficient delivery of the formulations to reach the lower respiratory tract. The amount of drug in small droplets (<5 μm), commonly described as the fine-droplet fraction, is the portion of an aerosolized drug most efficiently delivered to the distal airways. In some embodiments, droplet size of less than 5.0 μm is suitable, for example about 1.5 μm-5.0 μm, preferably droplet size of about 2.5 μm-3.5 μm or less.

In some embodiments, the fraction of droplets with size about 1.5 μm-5 μm is at least 20%, at least 30%, at least 40%, at least 50%, at least 60%, at least 70%, at least 80%, at least 90%, or more than 90% of total nebulized formulations. In some embodiments, the fraction of droplets with size about 2.5 μm-3.5 μm is at least 20%, at least 30%, at least 40%, at least 50%, at least 60%, at least 70%, at least 80%, at least 90%, or more than 90% of total nebulized formulations.

In some embodiments, formulations are delivered using a high efficiency jet nebulizer, a high efficiency ultrasonic nebulizer or a high efficiency vibrating mesh nebulizer, use of these devices enabling and/or enhancing the use of the reduced volume formulations of the invention. Many commercial nebulizers suitable for the administration of the formulations include, but not limited to NEBUTECH®, UP-DRAFT® II OPTI-NEB, PART LC® Plus, PAIR LC® Star, SIDESTREAM®. In preferred embodiments, the formulations are delivered by a high efficiency vibrating mesh nebulizer for example VOYAGER™ PRO, or OMRON® micro-air nebulizer (NE-U22V).

In some embodiments, formulations are for delivery with a high efficiency nebulizer, in particular one that can deliver at least 10%, preferably at least 20%, at least 30%, at least 40%, at least 50%, at least 60%, at least 70%, at least 80%, at least 90%, more than 90%, or approximately 100%, of the D-HAF formulations to the patient's lungs.

2. Inhalers

In some embodiments, the formulations of the present invention are designed for administration by inhalers. Inhalers are small, handheld devices that deliver a puff of medicine into the airways. There are three basic types: metered-dose inhalers (MDIs), dry powder inhalers (DPIs), and soft mist inhalers (SMI).

MDIs contain a liquid medication that is delivered as an aerosol spray. The medicine is held in a pressurized canister that has a metering valve. Patients close their lips around the mouthpiece or place the mouthpiece 1 to 2 inches from their mouth and breathe in slowly as they press down on the inhaler. An alternative method that many find preferable is to use a spacer. A spacer is a hollow plastic tube used between the mouthpiece and the canister of medicine. A spacer makes it easier to get the full dose of medication all the way to the lungs. In some embodiments, the amniotic fluid formulations are delivered by metered-dose inhalers.

A DPI is similar, but it releases a puff of dry powder instead of a liquid mist. DPIs should not be used with a spacer. Instead, patients close their mouth tightly around the mouthpiece of the DPI inhaler and inhale rapidly and steadily. In some embodiments, the amniotic fluid formulations are delivered by dry powder inhalers.

An SMI is a newer type of inhaler that provides a pre-measured amount of medicine in a slow-moving mist that helps inhale the medicine. Patients put their lips on the mouthpiece while holding the device horizontally and being careful not to cover the air vents. It actively delivers medicine in a way that does not depend on how fast one breathes in the air from the inhaler.

C. Dosages and Dosing Regimens

Dosage and dosing regimens are dependent on the severity of the lung disorder, and is known to those skilled in the art.

The formulation disclosed will be tailored to the individual subject, the nature of the condition to be treated in the subject, and generally, the judgment of the attending practitioner. In yet another embodiment, the formulation is any amount of about 0.1-10 ml combined with any amount of about 0.1-10 ml of sterile water, or saline solution.

For treatment of COPD and asthma, including, but not limited to, chronic bronchitis, emphysema, bronchiectasis, chronic bronchitis, interstitial lung disease, and alpha-1 antitrypsin emphysema using the disclosed formulations, it generally provides a nebulizer and an ampoule containing not less than 0.1 ml of the D-HAF formulation, for example, any amount between 0.1 ml to 10 ml of D-HAF mixed with sterile saline solution or sterile water.

A filled ampoule contains a formulation of D-HAF. This is generally in a pharmaceutically acceptable carrier and buffered for human use to a pH of about 3.5-10.0. The formulations of the examples are buffered to about pH 6.0-7.5.

The formulations are free of preservative, which is an advantage as some preservatives can be associated with bronchoconstrictor effects—the opposite effect to that required by the formulation. Water or saline solution is used to provide the carrier.

One or more tonicity adjusting agents may be added to provide the desired ionic strength. Tonicity-adjusting agents for use include those which display no or only negligible pharmacological activity after administration. Both inorganic and organic tonicity adjusting agents may be used. Compositions of the invention can also include excipients and/or additives. Examples of these are surfactants, stabilizers, complexing agents, antioxidants, or preservatives which prolong the duration of use of the finished pharmaceutical formulation, flavorings, vitamins, or other additives known in the art. Complexing agents include, but are not limited to, ethylenediaminetetraacetic acid (EDTA) or a salt thereof, such as the disodium salt, citric acid, nitrilotriacetic acid and the salts thereof. In one embodiment, the complexing agent is EDTA. Preservatives include, but are not limited to, those that protect the solution from contamination with pathogenic particles, including benzalkonium chloride or benzoic acid, or benzoates such as sodium benzoate. Antioxidants include, but are not limited to, vitamins, provitamins, ascorbic acid, vitamin E or salts or esters thereof.

In some embodiments, lyophilized D-HAF formulations are preferred. In some embodiments, the lyophilized D-HAF is reconstituted by adding the initial volume of water. In other embodiments, the formulation is further diluted to from about 1% to about 99% of the reconstituted D-HAF. The refrigerated formulation is readily diluted to from about 1% to about 99% of the original D-HAF to a desired concentration for applications.

In other embodiments, the final formulation is prepared as a much more concentrated solution depending on the need of application. For example, to minimize the amount of time patient needs to be confined to a nebulizer, a concentrated formulation is used to deliver the same effective dosage in a shorter period. In one embodiment, the lyophilized D-HAF is reconstituted by adding half of the initial volume of water to achieve twice as concentration solutions of all amniotic factors. In a further embodiment, the lyophilized D-HAF is reconstituted by adding 10% of the initial volume of water to achieve 10-fold more concentrated solutions of the amniotic factors for application. In some embodiments, the refrigerated D-HAF can be used to reconstitute the lyophilized D-HAF in order to obtain a more concentrated solution.

The D-HAF formulations can be administered as frequently as necessary and appropriate. The frequency generally depends on the severity of the lung damage, and the responsiveness of the target tissues to the treatment with D-HAF formulations. In some embodiments, the D-HAF formulations are administered on one-a-week basis. In other embodiments, the D-HAF formulations are administered on one-a-month basis. In some embodiments, the administration routine can change based on the practitioners assessment of the patient after the prior treatment.

D. Controls

The effect of amniotic fluid formulations on the lungs can be compared to a control. Suitable controls are known in the art. For example, in some embodiments, a subject treated with the D-HAF formulations are compared to a placebo-treated control subject who had similar symptoms as the experimental subject prior to treatment of the D-HAF formulations. In some embodiments, patients will perform self-evaluation within days, weeks, months after the initiation of the treatment based on their ability to copy with daily their abilities for example using Clinical COPD Questionnaire (CCQ). In some embodiments, subjects will be evaluated on regular intervals by attending physicians based on clinical scores such as FEV1, PEF scores, and their exercise tolerance, their reduction in inflammation in the affected area, and/or their baseline oxygen saturation.

The present invention will be further understood by reference to the following non-limiting examples.

EXAMPLES

Example 1: Treatment of COPD Patient with Amniotic Fluid Solution

The purpose of the study is to determine appropriate therapeutic treatment of COPD using nebulized amniotic fluid via vibrating mesh nebulizer.

Materials and Methods

Selection Criteria Patients must be free of cancer as determined by chest computerized tomography (CT) scans. In the case of cancer diagnosis in the past five year, there must be declaration of cancer-free by the treating physician. Patients must also be free of fibrotic disease. Patients must be free of tobacco usage within 6 months prior to the treatment.

Data Collection

Pulmonary function tests were performed at baseline (i.e. just prior to the treatment with the amniotic fluid formulation), at 1 month, and at 6 months. Spirometry data were collected at pre- and post-bronchodilation, 1 week, and 3 months. Oximetry data were collected whilst at rest with room-air at baseline, 30 minutes post treatment, 1 week, 1 month, 3 month, and 6 months. Oximetry data after 6-minute walk test with room air were collected at baseline, 1 week, 1 month, 3 months, 6 months. Blood pressure results were collected at every visit. All results were documented in patient-specific spreadsheet.

Dosage

PURAGEN®, the disclosed amniotic fluid formulation, was given at a dosage unit of 0.5 cc unless otherwise indicated. Typically, 0.5 cc PURAGEN® mixed in with 3.0 cc normal saline solution is added to a vibrating mesh nebulizer for administering to the patients. Routinely, only one-time treatment is given at the first visit followed by data collection at prescribed times including baseline, 1 month, 2 months, 3 months, etc., depending on the availability of the patients. If a physical visit to the clinic was not feasible an evaluation would be conducted over the phone. In more severe cases of COPD, a higher dose of PURAGEN® was given for example 1.0 cc. In some instances, additional doses were given.

Results

Treatment of Moderate-to-Severe COPD

Patient (C.T.) was diagnosed with COPD four years prior to the treatment. She had a persistent cough, shortness of breath, and poor skin color.

C.T. was given albuterol treatment, immediately followed by 0.5 cc PURAGEN® on the initial visit. At 2-week follow-up visit, C.T. appeared to have much improved skin color. C.T. said that since her initial treatment she had been generally much more active, such as carrying out daily activities of going to the mall, walking around the block and vacuuming her house without shortness of breath. She also mentioned that she only had one coughing spell since her treatment, which was remarkable since she was constantly coughing during her first visit. She no longer needed albuterol after her first visit, which she had not experienced in the past six months. Furthermore, C.T. showed a tremendous improvement in her CCQ (Clinical COPD Questionnaire) scores and reported overall improvement in her well-being.

C.T. highly praised PURAGEN® throughout her 2-week follow-up visit. Clinically she showed great improvement in her cough and her FEV1 was better than her baseline by 0.12, which was measured without any bronchodilation. She also showed a 10-point improvement in PEF score over her baseline. Her oxygenation stayed the same.

4-week follow-up evaluation was conducted over the phone. The patient reported to have continued improvement in her respiratory status. She said she was exercising more whilst still absent of cough. She mentioned that just prior to the phone conversation she vacuumed her house, washed her tile floors and dusted her house without any shortness of breath. She had not needed her bronchodilation since her initial visit to which she praised PURAGEN® as a miracle.

well-being and would like to further her improvement from further treatment. She also recognized that due to the severity of her condition, it would take longer to realize the gains from PURAGEN®. Clinically, she was the same as her initial visit. Her oxygenation stayed the same. However, she has not utilized her oxygen as much at home.

At four week follow-up, the patient reported increased exercise tolerance where she could exercise up to 20 minutes on the treadmill at 1.1 mph. Clinically, it was possible to obtain her FEV1 and PEF scores from her at this time point. She had also further reduced her CCQ scores. Additional doses of 0.5 cc PURAGEN® were further administered at week 4 and week 5.

At three month follow-up, the patient reported to be using more oxygen although her exercise levels remained the same. The patient described that PURAGEN® had not

TABLE 1

Summary for patient C.T.

| Time point | Pre-treatment | Pre-TX/Post Albuterol | Post treatment | Week 2 Follow-up | Change | Week 4 Follow-up | Change | 3 Month Follow-up | Change |
|---|---|---|---|---|---|---|---|---|---|
| FEV1 | 1.71 | 1.45 | 1.8 | 1.83 | 0.12 | via phone | | via phone | |
| PEF | 182 | 184 | 224 | 192 | 10 | via phone | | via phone | |
| $O_2$ Rest | 97 | 98 | 98 | 98 | 1 | via phone | | via phone | |
| $O_2$ Exercise | 98 | — | | | | | | | |
| Exercise time | 2 mins | 120 ft | | | | | | | |
| CCQ | 36 | | | 13 | −23 | 9 | −27 | 9 | −27 |
| Dose | | 0.5 cc | | | | | | | |

During the 3-month follow-up visit, the patient reported continued success on PURAGEN®. However, she did feel as if her improvement in her respiratory status had plateaued at this time point. She was given a second dose of 0.5 cc PURAGEN® the following day.

Treatment of Severe COPD

Patient (J.R.) was a 73-year old female diagnosed with COPD nine years prior to the treatment. The patient had suffered from severe COPD. J.R. had undergone treatment at the Lung Institute with no success or improvement. She routinely exercised three times per week; utilizing a treadmill for 8 mins, 8 mins, 8 mins, and 6 mins. She was given a prescription of 2 liters per minute (lpm) of oxygen for ambulation, and for night time when necessary. Her FEV1 and PEF could not be measured during this visit due to the severity of her condition. She received 1.0 ml PURAGEN® mixed with 2.0 ml of NaCl via a vibrating mesh nebulizer.

At the two-week follow-up visit, patient had improved skin color. It was determined that she had some improvement. Specifically, J.R. could exercise on the treadmill at 10 minute intervals compared to 8-minute intervals prior to the treatment. She had also reduced utilization of her oxygen at home—she was using it every morning for 15-20 minutes after waking up prior to the treatment but she had not used it since the first dose of PURAGEN®. She reported that her nasal passages had been chronically swollen but had not been swollen since her treatment. Her CCQ score, which evaluated her abilities to perform functions, was reduced from 39 at her initial visit to 19, indicating a significant improvement. J.R. reported overall improvement in her helped and might even be causing pain. However, based on clinical data of exercise tolerance, her condition had vastly improved.

TABLE 2

Summary for patient J.R.

| Time point | Pre-treatment | Pre-TX/Post Albuterol | Post treatment | Week 2 Follow-up | Change | Week 4 Follow-up | Change |
|---|---|---|---|---|---|---|---|
| FEV1 | 0 | 0 | 0 | 0 | 0 | 0.36 | 0.36 |
| PEF | 0 | 0 | 0 | 0 | 0 | 0.83 | 0.83 |
| $O_2$ Rest | 96 | 96 | 94 | 97 | 1 | 98 | 2 |
| $O_2$ Exercise | 84 | — | | | | | |
| Exercise time | 2 mins | 90 ft | | | | | |
| CCQ | 39 | | | 19 | −20 | 18 | −21 |
| Dose | | | 1.0 cc | | | 0.5 cc | |

Treatment of Asthma-induced COPD

Patient (M.R.) had a history of asthma with frequent wheezes. She suffered from asthma-induced COPD, and had been dependent on prednisone for a long time. She was very limited in her abilities to work, to walk, or to perform any muscle movements. She had also suffered from obstructive sleep apnea, and was using continuous positive airway pressure with 2.5 liters per minute (lpm) of oxygen at night. During daytime, she was given a prescription of administration of oxygen when necessary. She used bronchodilation with metered dose inhaler (MDI) 3 to 5 times a week. M.R. was also on nebulizer twice a day and she used her ancillary breathing muscles frequently.

One week after her initial treatment with PURAGEN®, she reported that she only used her rescue inhaler once. She had seen increase in her exercise tolerance, as well as a decrease in her prednisone dosage in agreement with physician's orders. She further reported that she had felt better in the mornings, whereas prior to the treatment waking up had always been a chore. Generally, she was also experiencing less shortness of breath. Her CCQ improved dramatically, reduced from 46 to 7. Her PEF and FEV1 remained the same. M.R. was administered a second dose of 0.5 cc PURAGEN® during her 2-week visit.

At the three-week follow-up visit, M.R.'s exercise tolerance and physiological markers both improved. Her prednisone usage was reduced to a half of pre-treatment usage. She had not required her asthma infusion for 2 months since her last infusion. A third dose of 0.5 ml PURAGEN® was given during this visit.

TABLE 3

Summary for patient M.R.

| Time point | Pre-treatment | Pre-TX/Post Albuterol | Post treatment | Week 2 Follow-up | Change | Week 3 Follow-up | Change |
|---|---|---|---|---|---|---|---|
| FEV1 | 0.61 | 0.63 | 0.6 | 0.58 | −0.03 | 0.64 | 0.03 |
| PEF | 162 | 157 | 160 | 135 | −27 | 175 | 13 |
| $O_2$ Rest | 98 | | | 95 | | 96 | |
| $O_2$ Exercise | 91 | | | | | 90 | |
| Exercise time | 2 min 27 sec | 240 ft | | | | 6 min; 950 ft | |
| CCQ | 46 | | | 7 | −39 | 6 | −40 |
| Dose | | | 0.5 cc | 0.5 cc | | 0.5 cc | |

Treatment of Severe Pulmonary Disease

Patient (B.B.) was a 71-year old male with severe pulmonary disease. CT scan showed significant scaring, but no active fibrotic disease process. The result indicated a combination of signs and symptoms of COPD, and possibly of reactive airway diseases. The patient was highly oxygen-dependent, using 3 liters per minute (lpm) of oxygen at rest, 4 liters per minute (lpm) of oxygen with ambulation and at night. He had also used noninvasive positive-pressure ventilation (NPPV) 10/6 for assistance when sleeping. Walk test revealed minimal exertion (42 ft) resulted in $O_2$ saturation of 88%, with resting $O_2$ saturation of 91%, both of which were measured whilst being administered $O_2$.

Just four days following the initial treatment, the patient called to report that his oxygenation had improved. Prior to the treatment, he had been hindered in carrying out activities of daily living due to shortness of breath. However, he reported that after the first treatment he was able to take off his oxygen to do self-care, which would usually result in his oxygen level to drop to 77% but it stayed at 88%.

At the two-week follow-up visit, the patient continued to improve his ADL abilities and experienced less oxygen desaturation in the absence of external supply of oxygen. At this time, the patient could stay off oxygen supply for 10 minutes before oxygen level dropped to 80%.

At the three-week follow-up visit, the patient further improved his ADL abilities as well as his exercise tolerance. The patient also had an increased PEF score, and a reduced CCQ score. Within three weeks following the initial treatment, the patient's spouse reported that B.B. had much improved well-being and could participate in much more physical activities such as going to the mall, and playing with their grandchild.

At the four-week follow-up visit, B.B. reported improved memory and prolonged activity time to about 20 min in the absence of external supply of oxygen. B.B. was also much less dependent on oxygen, dropping oxygen consumption to 50% compared to pre-treatment levels.

Seven weeks after initial visit, B.B. reported that he could be off oxygen for 40-50 min whilst active and 4 hours at rest.

At the nine-week follow-up visit, B.B. was significant improved than at the first visit. He could stay off oxygen for up to 4 hours whilst at rest, and up to 1 hour with activity. His ADLs were much improved—B.B. started off with not being able to perform any ADLs at the first visit and now he could perform ADLs without assistance, SOB, or fatigue. The patient could perform additional activities such as blowing bubbles with his grandchildren, doing yard maintenance, and light carpentry. Clinically, the improvement were observed in the following areas, 17% improvement in FEV1, 33% improvement in PEF, and 92% reduction in CCQ score (reduced score indicates greater ADLs and QOL), where PEF/FEV were performed without bronchodilation. In terms his oxygen requirement, his saturation levels were stable on room air, his supplemental $O_2$ dependency was reduced by 25%, and recovery time was shortened to less than 2 mins.

TABLE 4

Summary for patient B.B.

| Time point | Pre-treatment | Pre-TX/Post Albuterol | Post treatment | Week 2 Follow-up | Change | Week 3 Follow-up | Change | Week 4 Follow-up | Change |
|---|---|---|---|---|---|---|---|---|---|
| FEV1 | 1.43 | | 1.4 | 1.5 | 0.07 | 1.5 | 0.07 | 1.68 | 0.25 |
| PEF | 278 | | 214 | 280 | 2 | 349 | 71 | 369 | 91 |
| $O_2$ Rest | 91 | | 91 | 91 | | 88 | | | |
| $O_2$ Exercise | 88 | | | | | | | | |
| Exercise time | 0 min | 42 ft | | | | | | | |
| CCQ | 47 | | | | | 15 | −32 | | |
| Dose | 0.5 cc | | | 0.5 cc | | 0.5 cc | | | |

Treatment of Severe Persistent Asthma Patient (D.S.) was a 14-year old male with severe persistent asthma with acute exacerbations. He was diagnosed with asthma at the age of 4. Since then he always had occasional exacerbations and required daily pharmacological maintenance. D.S. was a track athlete and he used inhaler prior to, and/or post-track events. Since he was an active teenage, CCQ score and exercise test were not very informative in comparing pre- and post-treatment effects. Therefore, his race times and recovery were used to determine the effects of PURAGEN® treatment. After the initial dose of PURAGEN® received on the first visit, D.S. would only receive further doses if he was symptomatic.

In addition to the usual clinical scores, computed tomography (CT) scan was also performed on this patient. Contiguous contract and non-contrast enhanced axial CT images were obtained of the chest from the thoracic inlet through the lung bases with breath hold in expiration, pre- and post-therapy. Multiplanar reformatted images were generated and reviewed with both soft tissue and lung windows. 140 ml ULTRAVIST® 370. Contrast Volume Discarded: 0 ml. BUN/Creatinine not required.

Computed tomography findings were as follows:

1) Pre-therapy: there was anterior bowing of the posterior membranous trachea consistent with expiration; there was significant respiratory motion artifact which likely represented difficulty with breath holding and/or mild respiratory distress; there was mild hyperexpansion; evaluation of pulmonary vasculature was limited by respiratory motion artifact but grossly normal.

2) Post-therapy: there was anterior bowing of the posterior membranous trachea consistent with expiration; there was minimal respiratory motion artifact present only at the lung bases; the lungs were normally expanded; there was normal pulmonary vasculature.

3) The thyroid appeared normal. Minimal normal residual thymus was demonstrated. There was no axillary, mediastinal, or hilar lymphadenopathy. The airways were patent. There was no focal consolidation, pleural effusion or pneumothorax. There were no pulmonary nodules. The cardiac silhouette was normal without pericardial effusion. The aorta was normal in size. There was normal three-vessel anatomy. The pulmonary artery was normal in size.

4) Limited images through the upper abdomen demonstrated normal upper abdominal contents. Bone windows demonstrated no aggressive appearing osseous lesions. There was no scoliosis or spinal asymmetry. There were no vertebral body anomalies. The subcutaneous soft tissues appeared normal.

Radiologist/Physician interpreted that mildly hyperexpanded lungs with significant respiratory motion artifact was consistent with difficulty breath holding and/or mild respiratory distress in the pre-therapy scans; and normally expanded lungs with only minimal respiratory motion artifact was consistent with significant response to therapy in the post-therapy scans.

Four days after the treatment, D.S. reported that he had not had to use rescue inhaler since the initial visit. Furthermore, he did baseline running events without the need of bronchodilation pre- or post-events.

TABLE 5

Summary for patient D.S.

| Time point | Pre-treatment | Pre-TX |
|---|---|---|
| FEV1 | 2.61 | 2.83 |
| PEF | 359 | 383 |
| O₂ Rest | 98 | 98 |
| O₂ Exercise | N/A | |
| Exercise time | N/A | |
| CCQ | N/A | |
| Dose | | |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method of treating a lung disorder selected from asthma, chronic obstructive pulmonary disorder (COPD) or asthma-induced COPD in a subject, the method comprising:
   administering to the lung of the subject a sterile filtered de-cellularized human amniotic fluid (D-HAF) devoid of all amniotic stem cells, amniotic membrane particulate matter, chorion particles, and other undissolvables, and which is not heat-treated, chemical-treated, or irradiated, in an amount effective to provide one or more benefits to the lung to treat or alleviate the lung disorder or injury;
   wherein D-HAF is administered via a pulmonary, oropharyngeal, nasopharyngeal, and/or hypopharyngeal route;
   wherein the D-HAF is administered in the form of aerosol or with a nebulizer; and
   wherein the subject experiences a benefit of improved exercise endurance.

2. The method of claim 1 wherein the D-HAF is administered in a dosage unit between about 0.1 cc and about 10.0 cc.

3. The method of claim 1 wherein the D-HAF is diluted with sterile water, saline or buffer.

4. The method of claim 1 wherein the D-HAF is administered in the form of a high-efficiency jet nebulizer and/or high-efficiency ultrasonic nebulizer.

5. The method of claim 4 wherein the fraction of aerosolized droplets with a size of between about 1.5 µm and 5 µm, inclusive, is at least 50% of the formulation.

6. The method of claim 4 wherein the fraction of nebulized droplets with a size of between about 1.5 µm and 5 µm, inclusive, is at least 70% of the formulation.

7. The method of claim 1 wherein the D-HAF is administered via a high-efficiency vibrating mesh nebulizer or a breath-actuated nebulizer.

8. The method of claim 1 wherein the D-HAF is administered in combination with one or more therapeutic or diagnostic agents.

9. The method of claim 8 wherein the D-HAF is administered in combination with one or more agents selected from the group consisting of bronchodilators, corticosteroids, methylxanthines, phosphodiesterase-4 inhibitors, anti-angiogenesis agents, antimicrobial agents, antioxidants, anti-inflammatory agents, growth factors, immunosuppressant agents, anti-allergic agents, and combinations thereof.

10. The method of claim 1 wherein the lung disorder is selected from the group consisting of chronic obstructive pulmonary disorders (COPD) and asthma.

11. The method of claim 1 wherein the lung disorder is asthma-induced COPD.

12. The method of claim 1 wherein the D-HAF is in an amount effective to improve exercise endurance and reduce episodes of coughing and shortness of breath.

13. The method of claim 1 wherein the subject is a mammal.

14. The method of claim 13 wherein the mammal is selected from the group consisting of human, dog, cat, livestock, and race horses.

15. The method of claim 1 wherein the D-HAF is sterilized to a $10^{-6}$ sterility assurance level.

16. The method of claim 14 wherein the mammal is a human.

17. The method of claim 5 wherein the aerosolized droplets have a size of between 2.5 μm and 3.5 μm in diameter, inclusive.

* * * * *